United States Patent
Yoon et al.

(10) Patent No.: US 9,562,855 B1
(45) Date of Patent: Feb. 7, 2017

(54) DEVICES AND METHODS FOR DETECTION OF MICROORGANISMS VIA MIE SCATTERING

(75) Inventors: Jeong-Yeol Yoon, Tucson, AZ (US); David Jinsoo You, Tucson, AZ (US)

(73) Assignee: THE ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 1267 days.

(21) Appl. No.: 13/458,650

(22) Filed: Apr. 27, 2012

Related U.S. Application Data

(63) Continuation-in-part of application No. 12/630,069, filed on Dec. 3, 2009, now abandoned.
(Continued)

(51) Int. Cl.
*G01N 21/47* (2006.01)
*G01N 33/58* (2006.01)
(Continued)

(52) U.S. Cl.
CPC ........... *G01N 21/47* (2013.01); *B01L 3/502* (2013.01); *G01N 33/585* (2013.01);
(Continued)

(58) Field of Classification Search
CPC .......... A61B 5/0059; G01J 3/28; G01N 21/21; G01N 21/6445; G01N 21/6456; G01N 2800/52; G01N 33/5091
See application file for complete search history.

(56) References Cited

U.S. PATENT DOCUMENTS

| | | | |
|---|---|---|---|
| 4,174,952 A | * | 11/1979 | Cannell ............. G01N 21/47 250/574 |
| 4,521,521 A | | 6/1985 | Abbott et al. |

(Continued)

FOREIGN PATENT DOCUMENTS

WO  2008/049187 A1  5/2008

OTHER PUBLICATIONS

Heinze et al. "Microfluidic immunosensor for rapid and sensitive detection of bovine viral diarrhea virus", Sensors and Actuators B 138 (2009) 491-496.*
(Continued)

*Primary Examiner* — Erik B Crawford
(74) *Attorney, Agent, or Firm* — Nguyen & Tarbet Patent Law Firm

(57) ABSTRACT

Microfluidic methods and systems for detecting levels of microorganisms via Mie forward light scattering. The systems and methods of the present invention can be customized so as to optionally maximize scatter from the particle immunoagglutination and minimize that of the sample matrix, e.g., via selection of parameters particle diameter d, wavelength of incident λ, and/or scatter angle θ. Methods feature providing beads conjugated with an antibody specific for the microorganism, mixing beads with a sample to form a first mixture; providing a control mixture; irradiating the mixtures with incident light; detecting forward light scattering scattered by the first mixture at a first angle with respect to the incident light and forward scattered light scattered by the control the same first angle with respect to the incident light; determining I and $I_0$ from the light scattering; comparing I with $I_0$; and determining a level of the microorganism.

3 Claims, 28 Drawing Sheets

Related U.S. Application Data

(60) Provisional application No. 61/479,700, filed on Apr. 27, 2011, provisional application No. 61/623,966, filed on Apr. 13, 2012.

(51) Int. Cl.
  *B01L 3/00* (2006.01)
  *G01N 33/569* (2006.01)

(52) U.S. Cl.
  CPC . *B01L 2300/0816* (2013.01); *G01N 33/56911* (2013.01); *G01N 2021/4704* (2013.01); *G01N 2021/4707* (2013.01); *G01N 2021/4711* (2013.01)

(56) References Cited

U.S. PATENT DOCUMENTS

| | | | |
|---|---|---|---|
| 5,862,273 A | 1/1999 | Pelletier | |
| 5,943,130 A | 8/1999 | Bonin et al. | |
| 6,040,906 A | 3/2000 | Harhay | |
| 6,689,572 B1 | 2/2004 | Huang et al. | |
| 7,034,325 B2 | 4/2006 | Bestesty et al. | |
| 7,118,676 B2 | 10/2006 | Mueth et al. | |
| 7,300,631 B2 | 11/2007 | Miller et al. | |
| 7,338,813 B2 | 3/2008 | Obana | |
| 7,576,861 B2 | 8/2009 | Gilbert et al. | |
| 7,738,099 B2 | 6/2010 | Morrell et al. | |
| 2002/0064867 A1 | 5/2002 | Clark et al. | |
| 2002/0180963 A1 | 12/2002 | Chien et al. | |
| 2004/0056197 A1 | 3/2004 | Davidson et al. | |
| 2006/0129327 A1 | 6/2006 | Kim et al. | |
| 2006/0172370 A1 | 8/2006 | Hirleman et al. | |
| 2007/0279627 A1 | 12/2007 | Tack et al. | |
| 2008/0032281 A1 | 2/2008 | Lea et al. | |
| 2010/0136610 A1 | 6/2010 | Yoon et al. | |
| 2011/0207152 A1 | 8/2011 | Shen et al. | |

OTHER PUBLICATIONS

Lucas et al., "Lab-on-a-chip immunoassay for multiple antibodies using microsphere light scattering and quantum dot emission", Aug. 11, 2007, Biosensors & Bioelectronics, 23, pp. 675-681.

Lucas et al., "Latex immunoagglutination assay for a vasculitis market in a microfluidic device using static light scattering detection", Dec. 1, 2006, Biosensors and Bioelectronics, 22, pp. 2216-2222.

Han et al., Single cell level detection of *Escherichia coli* in microfluidic device, Biosensors and Biolectronics, vol. 23, No. 8, pp. 1303-1306 [online], Dec. 4, 2007 (Dec. 4, 2007), Retriefed from the internet: www.sciencedirect.com.

Han (2007) Analytica Chimica Acta 584: 252-259.

\* cited by examiner $$i_1 = \left| \sum_{n=1}^{\infty} \frac{2n+1}{n(n+1)} (a_n \pi_n \cos\theta + b_n \tau_n \cos\theta) \right|^2$$

$$i_2 = \left| \sum_{n=1}^{\infty} \frac{2n+1}{n(n+1)} (a_n \tau_n \cos\theta + b_n \pi_n \cos\theta) \right|^2$$

FIG. 15A $$a_n = \frac{\psi_n(z)}{\zeta_n(z)} A_n \qquad b_n = \frac{\psi_n(z)}{\zeta_n(z)} B_n$$

FIG. 15B $$\zeta_n(z) = \sqrt{\frac{\pi z}{2}} \left[ J_{n+1/2}(z) + i Y_{n+1/2}(z) \right]$$

$$\psi_n(z) = \sqrt{\frac{\pi z}{2}} J_{n+1/2}(z)$$

FIG. 15C

DEVICES AND METHODS FOR DETECTION OF MICROORGANISMS VIA MIE SCATTERING

CROSS REFERENCE

This application is a continuation-in-part of U.S. patent application Ser. No. 12/630,069 filed Dec. 3, 2009 and claims priority to U.S. Provisional Application Ser. No. 61/479,700 filed Apr. 27, 2011 and U.S. Provisional Application Ser. No. 61/623,966 filed Apr. 13, 2012, the disclosures of which are incorporated herein by reference in their entirety.

FIELD OF THE INVENTION

The present invention is directed to methods and devices for detection of microorganisms, more particularly to devices and methods for detecting Mie forward light scattering of the microorganisms and antibody-conjugated beads.

BACKGROUND OF THE INVENTION

Illnesses caused by foodborne pathogens range from mild gastrointestinal infections to life-threatening hemorrhagic colitis, haemolytic uremic syndrome, and thrombotic thrombocytopenic purpura. Outbreaks of foodborne pathogens have recently increased in fresh produce. Conventional detection methods often require sample preparation (cell lysis and filtration) and concentration (cell culturing), which can be time consuming.

The present invention features methods and devices (e.g., microfluidic methods and microfluidic devices) for detecting microorganisms via Mie scattering. The devices may be hand-held and highly portable. As used herein, the term "microorganisms" includes bacteria, archaea, protists, fungi, microscopic plants (e.g., algae), microscopic animals (e.g., plankton), and viruses. For example, an embodiment wherein a device detects a microorganism includes a device that detects a bacteria or a virus, etc. The devices of the present invention may quantify increased light scattering due to immunoagglutination (e.g., immunoagglutination in a sample in the device).

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

The present invention features methods and systems, e.g., microfluidic systems, for detecting levels of microorganism. The systems and methods of the present invention can be customized so as to optionally maximize scatter from the particle immunoagglutination and minimize that of the sample matrix, e.g., via selection of parameters particle diameter d, wavelength of incident A, and/or scatter angle θ.

The present invention features methods of detecting a level of a microorganism.

In some embodiments, the method comprises (a) providing a first bead suspension comprising microparticle beads conjugated with an antibody specific for a first microorganism; (b) mixing the first bead suspension with a portion of a sample to form a first mixture, the sample being tested for the presence of the first microorganism; (c) providing a second mixture, the second mixture being a control; (d) introducing the first mixture to a first test region of a slide and introducing the second mixture to a second test region of the slide; (e) irradiating simultaneously the first mixture and the second mixture with an incident light, the irradiating is performed either at the same time or without movement of the slide in between irradiating the first mixture and the second mixture; (f) detecting simultaneously (i) a forward scattered light scattered by immunoagglutination of a combination of the first microorganisms and the antibodies specific for the first microorganism on the microparticle beads in the first mixture, the forward scattered light is Mie scattering at a first angle with respect to the incident light, the first angle being a particular angle between about 30 to 60 degrees, and (ii) a forward scattered light scattered by the second mixture, the forward scattered light is Mie scattering at a second angle with respect to the incident light, the first angle and the second angle being the same angle; (g) determining I from the scattering of (f)-(i) and determining $I_0$ from the scattering of (f)-(ii); and (h) comparing I with $I_0$ and configuring I and $I_0$ to represent the level of the microorganism.

In some embodiments, the method comprises: (a) providing a system comprising (i) a housing having a testing cavity; (ii) a test slide insertable into the testing cavity of the housing, the test slide comprises a first channel and a second channel, both channels have an inlet adapted to accept a mixture, a first test region is disposed in the first channel and a second test region is disposed in the second channel; (iii) a light device disposed in the housing, the light device emits an incident light through both the first test region and the second test region; and (iv) a light detection component disposed in the housing, the light detection component detects light scattered in the first test region at a first angle and light scattered in the second test region at a second angle, the second angle being the same as the first angle; (b) providing a first bead suspension comprising microparticle beads conjugated with an antibody specific for a first microorganism; (c) mixing the first bead suspension with a portion of a sample to form a first mixture, the sample being tested for the presence of the first microorganism; (d) providing a second mixture, the second mixture being a control; (e) inserting the first mixture into the inlet of the first channel and inserting the second mixture into the inlet of the second channel; (f) the light irradiating the first mixture in the first test region and the second mixture in the second test region with incident light; (g) the light detection component detecting (i) a forward scattered light scattered by immunoagglutination of a combination of the first microorganisms and the antibodies specific for the first microorganism on the microparticle beads in the first mixture, the forward scattered light is Mie scattering at a first angle with respect to the incident light, and (ii) a forward scattered light scattered by the second mixture, the forward scattered light is Mie scattering at a second angle with respect to the incident light, the first angle and the second angle being the same angle; (h) the system 100 determining I from the scattering of (g)-(i) and determining $I_0$ from the scattering of (g)-(ii); and (f) the system comparing/with $I_0$ and configuring I and $I_0$ to represent the level of the microorganism.

In some embodiments, the method comprises: (a) providing a system comprising (i) a housing having a testing cavity; (ii) a test slide insertable into the testing cavity of the housing, the test slide comprises a first channel and a second channel, both channels share an inlet, the inlet is adapted to accept a sample, a first test region is disposed in the first channel and a second test region is disposed in the second channel, a first lyophilized portion of microparticles is disposed in the first channel in between the inlet and the first test region, the first lyophilized portion of microparticles comprises a lyophilized portion of microparticles conjugated with an antibody specific for the microorganism; (iii) a light device disposed in the housing, the light device emits an incident light through both the first test region and the second test region; and (iv) a light detection component disposed in the housing, the light detection component detects light scattered in the first test region at a first angle and light scattered in the second test region at a second angle, the second angle being the same as the first angle; (b) inserting a sample into the inlet, the sample diffuses through both the first channel and the second channel, the sample in the first channel mixes with the first lyophilized portion of microparticles and travels to the first test region, the sample in the second channel travels to the second test region; (c) the light irradiating the first test region and the second test region with incident light; (d) the light detection component detecting (i) a forward scattered light scattered by sample in the first test region, the forward scattered light is Mie scattering at a first angle with respect to the incident light, and (ii) a forward scattered light scattered by the sample in the second test region, the forward scattered light is Mie scattering at a second angle with respect to the incident light, the first angle and the second angle being the same angle; (e) the system determining I from the scattering of (d)-(i) and determining $I_0$ from the scattering of (d)-(ii); and (f) the system comparing I with $I_0$ and configuring I and $I_0$ to represent the level of the microorganism. In some embodiments, step (f) comprises irradiating the first test region and the second test region at the same time, and step (g) comprises detecting scattered light from the first test region 170a and the second test region at the same time. In some embodiments, step (f) comprises irradiating the first test region and the second test region serially, wherein the test slide is not moved in between irradiating the first test region and second test region, and step (g) comprises detecting scattered light from the first test region and the second test region serially, wherein the test slide is not moved in between detecting scattered light from the first test region and the second test region.

The present invention also features systems for detecting a level of a microorganism.

In some embodiments, the system comprises (a) a housing having a testing cavity; (b) a test slide insertable into the testing cavity of the housing, the test slide comprises a first channel and a second channel, a first test region is disposed in the first channel and a second test region is disposed in the second channel; (c) a first light device and a second light both disposed in the housing, the first light device emits a first incident light through the first test region and the second light device emits a second incident light through the second test region; and (d) a first light detection component and a second light detection component both disposed in the housing, the first light detection component is at an angle with respect to the first test region such that the first light detection component detects light scattered in the first test region at a first angle and the second light detection component is at an angle with respect to the second test region such that the second light detection component detects light scattered in the second test region at a second angle, the first angle being the same as the second angle.

In some embodiments, the system comprises (a) a housing having a testing cavity; (b) a test slide insertable into the testing cavity of the housing, the test slide comprises a first channel and a second channel, a first test region is disposed in the first channel and a second test region is disposed in the second channel; (c) a light device disposed in the housing, the light device emits an incident light through both the first test region and the second test region; and (d) a light detection component disposed in the housing, the light detection component detects light scattered in the first test region at a first angle and light scattered in the second test region at a second angle, the second angle being the same as the first angle.

In some embodiments, the microorganism is a bacteria, an archaea, a protist, a fungus, a microscopic plant, a microscopic animal, or a virus.

In some embodiments, the microparticle beads each have a particular diameter between about 500 nm to about 920 nm. In some embodiments, the microparticle beads each have a diameter of about 920 nm. In some embodiments, the microparticle beads are constructed from a material comprising polystyrene. In some embodiments, the microparticle beads comprise a plurality of carboxyl groups disposed on an outer surface. In some embodiments, the microparticle beads comprise at least 5 carboxyl groups per $nm^2$ surface area. In some embodiments, the carboxyl groups comprise polyacrylic acid (PAA) or polymethacrylic acid (PMAA).

In some embodiments, the second mixture comprises a second bead suspension comprising microparticle beads that are not conjugated with the antibody specific for the first microorganism. In some embodiments, the second mixture comprises a suspension of the antibody specific for the first microorganism, the antibody specific for the first microorganism is not conjugated to microparticle beads.

In some embodiments, the incident light has a wavelength between about 320 to 800 nm. In some embodiments, the incident light has a wavelength of about 650 nm. In some embodiments, the first angle is a particular angle between 30 and 60 degrees. In some embodiments, the first angle is a particular angle between 20 and 70 degrees. In some embodiments, the first angle is a particular angle between 40 and 50 degrees. In some embodiments, the first angle is 44 degrees. In some embodiments, the first angle is 45 degrees. In some embodiments, the first angle is 46 degrees. In some embodiments, the first angle is at least 5 degrees less or 5 degrees more than a maximum scattering angle of a sample matrix, the sample matrix being the sample in its whole form.

In some embodiments, the light device (or the first light device and second light device) irradiates the first test region and the second test region, respectively, at the same time, and the light detection component detects scattered light from the first test region and the second test region, respectively, at the same time. In some embodiments, the light device (or the first light device and second light device) irradiates the first test region and the second test region, respectively, serially, wherein the test slide is not moved in between irradiating the first test region and second test region, and the light detection component (or the first light detection component and the second light detection component) detects scattered light from the first test region and the second test region, respectively, serially, wherein the test slide is not moved in between detecting scattered light from the first test region and the second test region.

In some embodiments, the system comprises a first beam splitter and a light conduit operatively connected to the first beam splitter, the first beam splitter is adapted to split light emitted from the light device, a first arm of the light conduit directs light emitted from the light device to the first test region and a second arm of the light conduit directs light emitted from the light device to the second test region. In some embodiments, the system comprises a switch for selectively allowing and preventing light being directed to the first test region via the first arm of the light conduit and light being directed to the second test region via the second arm of the light conduit. In some embodiments, the system comprises a second beam splitter and a light conduit operatively connected to the second beam splitter, a first arm of the light conduit accepts scattered light from the first test region, a second arm of the light conduit accepts scattered light from the second test region, the second beam splitter accepts the scattered light from the first arm and the second arm of the light conduit and delivers said scattered light to the light detection component. In some embodiments, the light conduit comprises an optical fiber or a light pipe.

In some embodiments, the testing cavity is optically isolated from the housing. In some embodiments, the testing cavity is thermally isolated from the housing. In some embodiments, the light (or the first light and the second light) is disposed in the testing cavity of the housing.

In some embodiments, a tray is disposed in the testing cavity, the tray is adapted to accept the test slide. In some embodiments, both channels comprise an inlet and an outlet, inlets are adapted to accept mixtures. In some embodiments, the mixtures are inserted into the inlets via a syringe. In some embodiments, both channels share an inlet and both channels have a separate outlet, the inlet is adapted to accept a sample. In some embodiments, the sample is inserted into the inlet via a syringe.

In some embodiments, the channels are about 1.0 mm in width. In some embodiments, the channels are between about 0.25 and 1.5 mm in width. In some embodiments, the channels are about 80 μm in depth. In some embodiments, the channels are between about 20 and 150 μm in depth.

In some embodiments, the light device is a laser diode. In some embodiments, the first light device and the second light device are each laser diodes. In some embodiments, the first light device and the second light device are arranged parallel to each other. In some embodiments, the light device comprises a laser diode and a collimating lens. In some embodiments, the first light device comprises a first laser diode and a first collimating lens, and the second light device comprises a second laser diode and a second collimating lens.

In some embodiments, the light detection component (or the light detection components) is a photodiode (e.g., avalanche photodiode). In some embodiments, signals detected by the light detection component (or light detection components) are differential voltage signals. In some embodiments, the light detection components (or the light detection components) is mounted at a fixed angle, e.g., 45 degrees, between 30 to 60 degrees, between 20 and 70 degrees, etc. In some embodiments, the angle (or the first angle and the second angle) is 45 degrees. In some embodiments, the angle (or the first angle and the second angle) is a particular angle between 30 and 60 degrees. In some embodiments, the angle (or the first angle and the second angle) is a particular angle between 20 and 70 degrees.

In some embodiments, the light device and light detection component is enclosed in the testing cavity of the housing. In some embodiments, each of the first light device, the second light device, the first light detection component, and the second light detection component are enclosed in the testing cavity of the housing. In some embodiments, the light detection component (or light detection components) is fixedly mounted in a first cartridge, the first cartridge is removably disposed in the housing.

In some embodiments, the system comprises a processor system operatively connected to the light device (or light devices) and the light detection component (or light detection components). In some embodiments, the processor system comprises a microprocessor. In some embodiments, the microprocessor is configured to calculate an I value from a first input signal from the light detection component (or the first light detection component) and an $I_0$ value from a second input signal from the light detection component (or the second light detection component).

In some embodiments, the microprocessor is configured to convert the I value and the $I_0$ value to one or more of: a ratio of $I/I_0$, a difference between I and $I_0$, and a level of microorganism.

In some embodiments, the system comprises a differential operational amplifier circuit operatively connecting the light detection component (or light detection components) to the microprocessor, the differential operational amplifier circuit amplifies signals detected by the light detection component (or light detection components). In some embodiments, the differential operational amplifier is a quadruple op-amp LM324. In some embodiments, the system comprises an analog-to-digital converter (ADC) operatively connected to the microprocessor. In some embodiments, the ADC is a 24-bit ADC. In some embodiments, the system comprises a display component operatively connected to the ADC, the display component displays at least one of: a ratio of $I/I_0$, a difference between I and $I_0$, and a level of microorganism.

In some embodiments, a first lyophilized portion of microparticles is disposed in the first channel in between the inlet and the first test region, the first lyophilized portion of microparticles comprises a lyophilized portion of microparticles conjugated with an antibody specific for a microorganism. In some embodiments, a second lyophilized portion of microparticles is disposed in the second channel in between the inlet and the second test region. In some embodiments, the second lyophilized portion of microparticles comprises a lyophilized portion of microparticles that are not conjugated with an antibody (e.g., antibody specific for the microorganism). In some embodiments, the second lyophilized portion of microparticles comprises a lyophilized antibody (e.g., antibody specific for the microorganism) that is not conjugated to a bead.

In some embodiments, a detergent (e.g., polysorbate detergent) is disposed in the first channel in between the inlet and the first lyophilized portion of microparticles. In some embodiments, a detergent (e.g., polysorbate detergent) is disposed in the second channel in between the inlet and the second test region. In some embodiments, a detergent (e.g., polysorbate detergent) is disposed in the second channel in between the inlet and the second lyophilized portion of microparticles.

In some embodiments, the level of the microorganism is a CFU per volume unit or a CFU per mass unit. In some embodiments, the CFU per volume unit is CFU/ml. In some embodiments, the CFU per mass unit is CFU/g. In some embodiments, the level of the microorganism is in colony forming units per ml (CFU/ml).

In some embodiments, the method comprises (a) plotting a first Mie light scattering curve of light scattering intensity versus forward scattering angle at a wavelength $\lambda_1$ for a sample matrix by providing sample matrix parameters and processing the sample matrix parameters in a standard Mie scattering equation, the sample matrix parameters include at least a particle diameter $d_1$ for the sample matrix, a particle concentration $\phi_1$ for the sample matrix, and a refractive index $n_1$ for the sample matrix, the first Mie light scattering curve comprises a first maximum light scattering intensity at a first maximum scattering angle; (b) plotting a second Mie light scattering curve of light scattering intensity versus forward scattering angle at the wavelength $\lambda_1$ for unbound microparticles by providing unbound microparticle parameters and processing the unbound microparticle parameters in the standard Mie scattering equation, the unbound microparticle parameters include at least a particle diameter $d_2$ for the unbound microparticles, a particle concentration $\phi_2$ for the unbound microparticles, and a refractive index $n_2$ for the unbound microparticles, the second Mie light scattering curve comprises a second maximum light scattering intensity at a second maximum scattering angle; (c) plotting a third Mie light scattering curve of light scattering intensity versus forward scattering angle at the wavelength $\lambda_1$ for agglutinated microparticles by providing agglutinated microparticle parameters and processing the agglutinated microparticle parameters in the standard Mie scattering equation, the agglutinated microparticle parameters include at least a particle diameter $d_3$ for the agglutinated microparticles, a particle concentration $\phi_3$ for the agglutinated microparticles, and a refractive index $n_2$ for the agglutinated microparticles, the third Mie light scattering curve comprises a third maximum light scattering intensity at a third maximum scattering angle; (d) comparing the first Mie light scattering curve, the second Mie light scattering curve, and the third Mie light scattering curve, wherein the wavelength $\lambda_1$ and the particle diameter $d_2$ are selected so as to yield an angle $\theta_1$, angle $\theta_1$ being an angle on the third Mie light scattering curve that has a light scattering intensity that is greater than both a light scattering intensity of the first Mie light scattering curve at angle $\theta_1$ and a light scattering intensity of the second Mie light scattering curve at angle $\theta_1$; (e) mixing a sample with unbound microparticles to create a first mixture of agglutinated microparticles; (f) providing a second mixture, the second mixture being a control; (g) irradiating the first mixture with incident light having the wavelength $\lambda_1$ and irradiating the second mixture with incident light having the wavelength $\lambda_1$; (h) detecting a relative intensity of forward scattered light scattered by the first mixture (I) at angle $\theta_1$ and a relative intensity of forward scattered light scattered by the second mixture ($I_0$) at angle $\theta_1$; and (i) configuring I and $I_0$ to represent the level of the microorganism.

In some embodiments, the wavelength $\lambda_1$ and the particle diameter $d_2$ are selected so as to yield an angle $\theta_1$, angle $\theta_1$ being an angle on the third Mie light scattering curve that has a light scattering intensity that is at least 25% greater than both a light scattering intensity of the first Mie light scattering curve at angle $\theta_1$ and a light scattering intensity of the second Mie light scattering curve at angle $\theta_1$. In some embodiments, the wavelength $\lambda_1$ and the particle diameter $d_2$ are selected so as to yield an angle $\theta_1$, angle $\theta_1$ being an angle on the third Mie light scattering curve that has a light scattering intensity that is at least 50% greater than both a light scattering intensity of the first Mie light scattering curve at angle $\theta_1$ and a light scattering intensity of the second Mie light scattering curve at angle $\theta_1$. In some embodiments, the wavelength $\lambda_1$ and the particle diameter $d_2$ are selected so as to yield an angle $\theta_1$, angle $\theta_1$ being an angle on the third Mie light scattering curve that has a light scattering intensity that is at least 100% greater than both a light scattering intensity of the first Mie light scattering curve at angle $\theta_1$ and a light scattering intensity of the second Mie light scattering curve at angle $\theta_1$. In some embodiments, the wavelength $\lambda_1$ and the particle diameter $d_2$ are selected so as to yield an angle $\theta_1$, angle $\theta_1$ being an angle on the third Mie light scattering curve that has a light scattering intensity that is at least 150% greater than both a light scattering intensity of the first Mie light scattering curve at angle $\theta_1$ and a light scattering intensity of the second Mie light scattering curve at angle $\theta_1$.

In some embodiments, angle $\theta_1$ is different than the first maximum scattering angle of the sample matrix and the second maximum scattering angle of the unbound microparticles. In some embodiments, angle $\theta_1$ is both (a) at least 5 degrees more or 5 degrees less than the first maximum scattering angle of the sample matrix and (b) at least 5 degrees more or 5 degrees less than the second maximum scattering angle of the unbound microparticles. In some embodiments, angle $\theta_1$ is both (a) at least 4 degrees more or 4 degrees less than the first maximum scattering angle of the sample matrix and (b) at least 4 degrees more or 4 degrees less than the second maximum scattering angle of the unbound microparticles. In some embodiments, angle $\theta_1$ is both (a) at least 3 degrees more or 3 degrees less than the first maximum scattering angle of the sample matrix and (b) at least 3 degrees more or 3 degrees less than the second maximum scattering angle of the unbound microparticles.

In some embodiments, the refractive index $n_2$ is 1.59. In some embodiments, the particle diameter $d_2$ is 0.920 μm and the particle diameter $d_3$ is between 1.6 and 1.7. In some embodiments, the particle concentration $\phi_3$ for the agglutinated microparticles is about ⅓ the particle concentration $\phi_2$ for the unbound microparticles. In some embodiments, the particle diameter $d_1$ for the sample matrix is calculated by analyzing microscopic images of the sample matrix.

In some embodiments, the particle diameter $d_2$ is between about 500 to 1000 nm. In some embodiments, the wavelength $\lambda_1$ is between about 100 to 700 nm. In some embodiments, the wavelength $\lambda_1$ is about 650 nm.

BRIEF DESCRIPTION OF THE DRAWINGS

FIG. 1 is a schematic representation of antibody conjugation to a bead (e.g., microsphere). The bead 210 is conjugated with antibodies 220, forming a conjugated particle.

FIG. 2 is a schematic representation of immunoagglutination from mixing a target (e.g., microorganism) and antibody-conjugated beads. The microorganism-specific antibodies 220 of the conjugated particles bind a microorganism 205, causing agglutination.

FIG. 3 shows a microfluidic slide with two channels (e.g., the test channel and the control channel). The mixtures (e.g., first mixture and second mixtures) are prepared prior to insertion into the test slide. The first mixture is added to the first test channel (test channel) and the second mixture (control mixture) is added to the second test channel (control channel).

FIG. 4 shows a simulation experiment of the Mie scattering properties of filtered lettuce particles, 920 nm microparticles as singlets representing a sample without the microorganism (e.g., no agglutination) and 920 nm microparticles as triplets representing a sample with the microorganism (e.g., agglutination).

FIG. 5A is a perspective view of a microfluidic system for detecting microorganisms in samples.

FIG. 5B is a detailed (internal) view of the system of FIG. 5A.

FIG. 5C is a detailed view of the testing cavity of the housing of the system of FIG. 5A.

Figure 10:
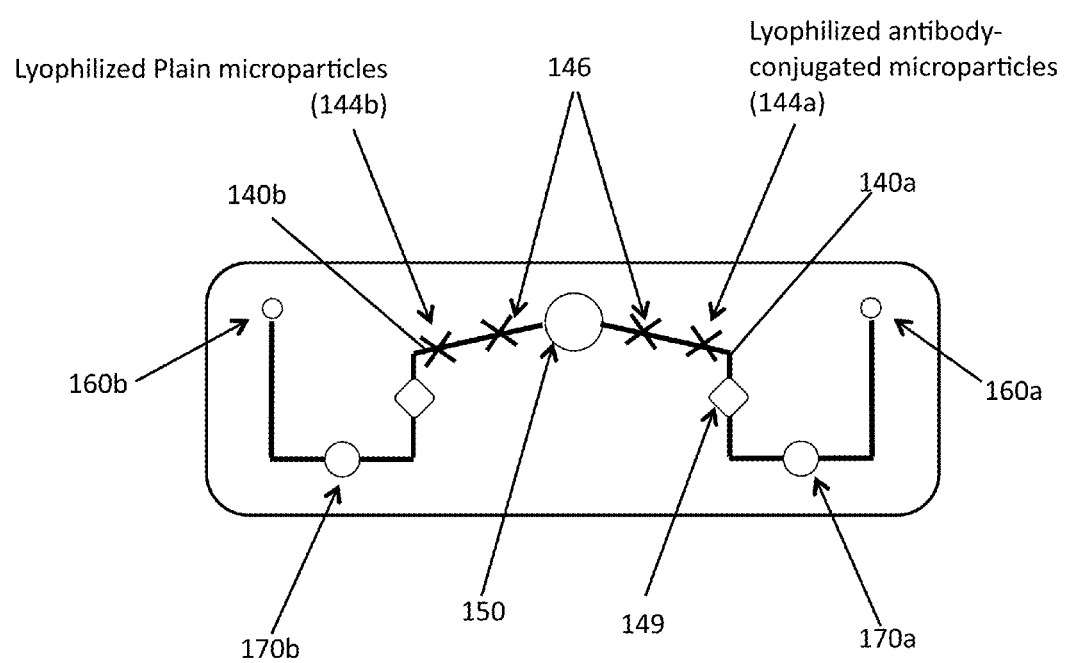

FIG. 10 shows a microfluidic slide with a central inlet for insertion of the sample. A sample is loaded into the central inlet and splits into 2 channels, one with antibody-conjugated microparticles and the other with plain particles (non-antibody-conjugated), both vacuum-dried in the channels. Pre-mixing of the sample with another component may not be necessary.

Figure 11A:
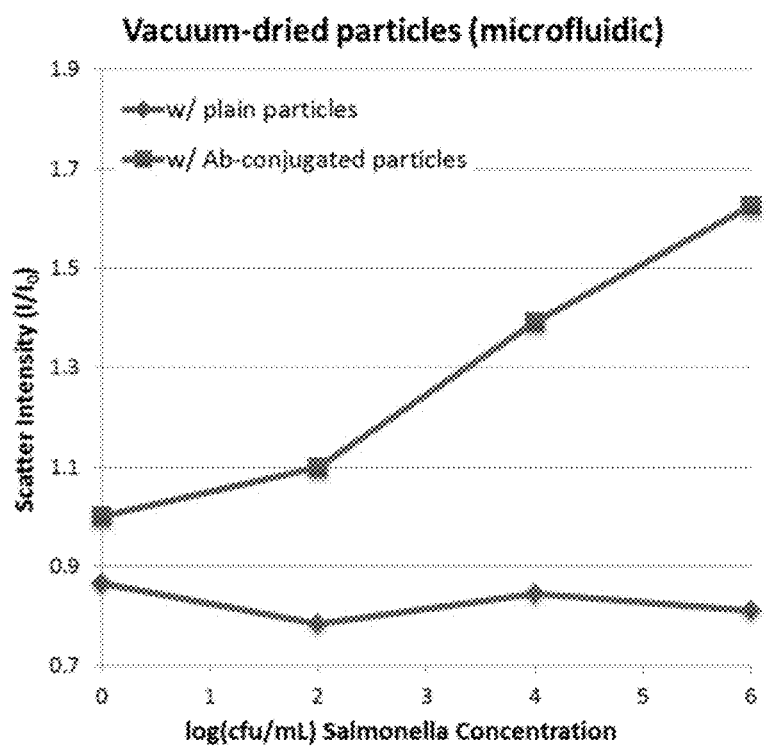

FIG. 11A shows results using the microfluidic slide of FIG. 10. Normalized light scatter intensities can be obtained with single sample loading, without using a negative control (PBS). Standard error=0.12-0.19.

Figure 11B:
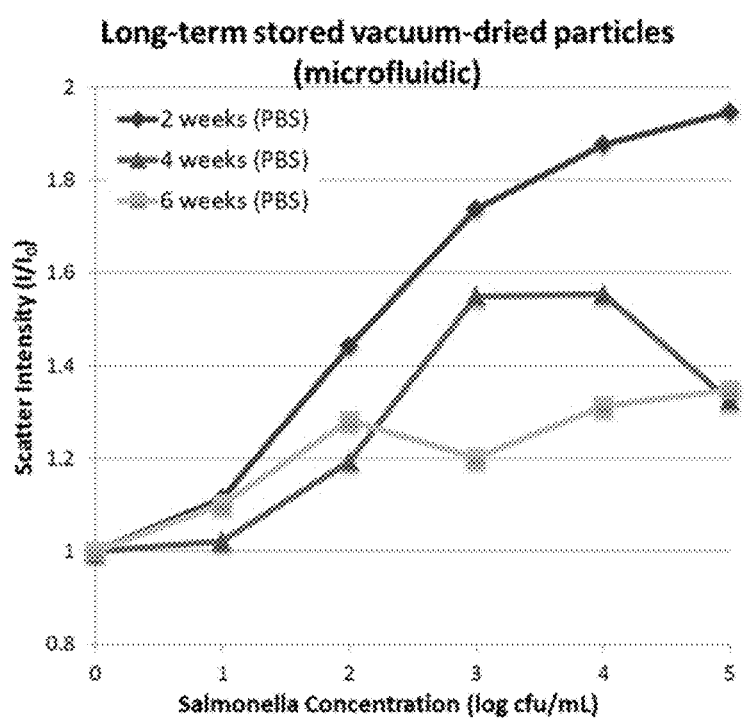

FIG. 11B shows the experiment performed with a microfluidic slide with vacuum-dried particles that were stored for 2, 4 and 6 weeks at room temperature, showing signal decrease with higher concentrations from gradual antibody denaturation.

Figure 12:
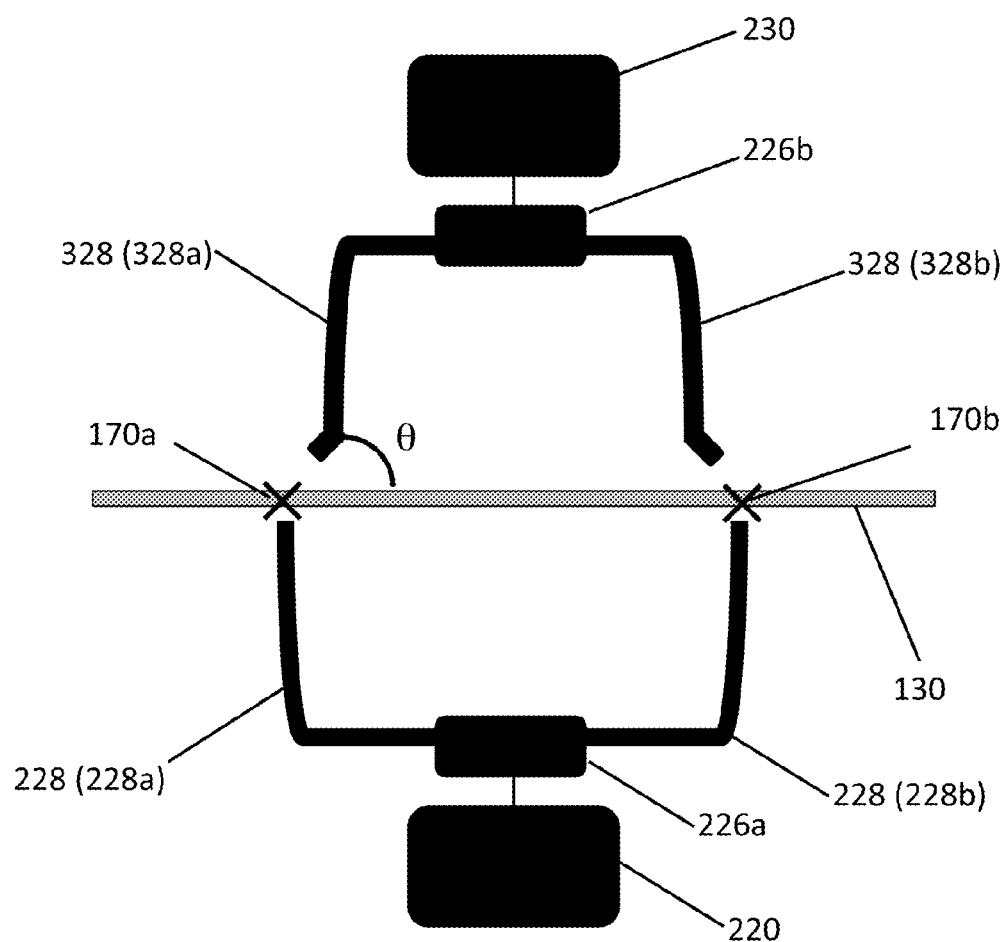

FIG. 12 is a schematic representation of a microfluidic system comprising a single light device and a single light detection component.

Figure 13:
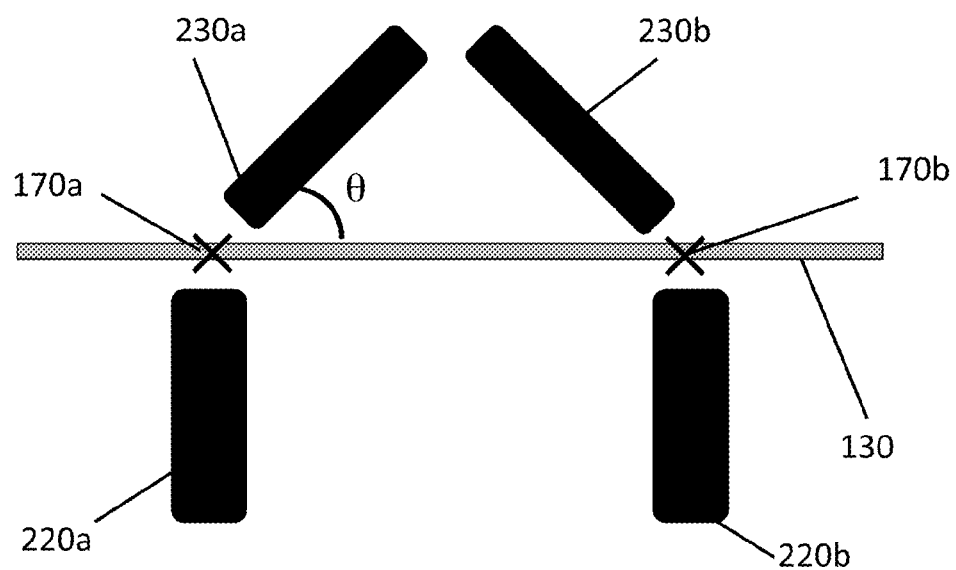

FIG. 13 is a schematic representation of a microfluidic system comprising two light devices and two light detection components.

Figure 14A:
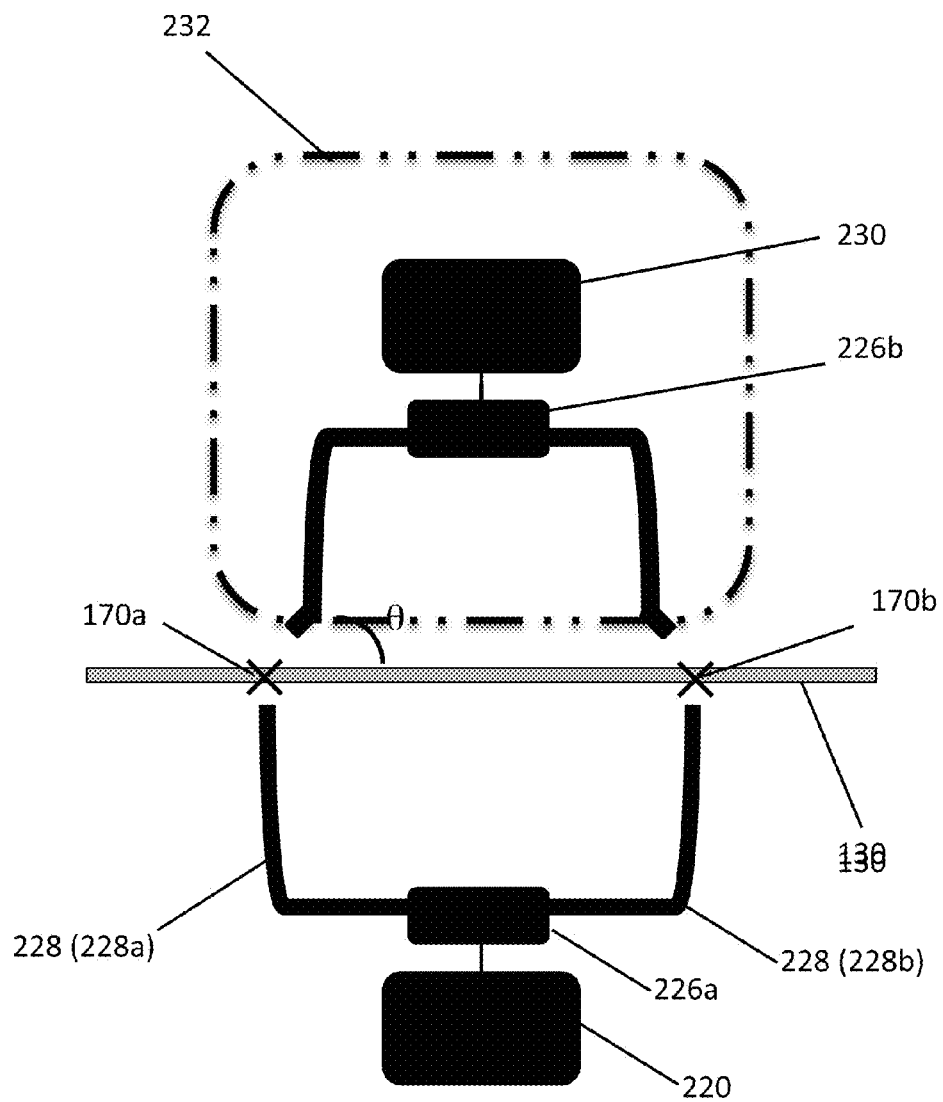

FIG. 14A is a schematic representation of a microfluidic system comprising a single light device and a single light detection component, wherein the light detection component is mounted on a removable cartridge.

Figure 14B:
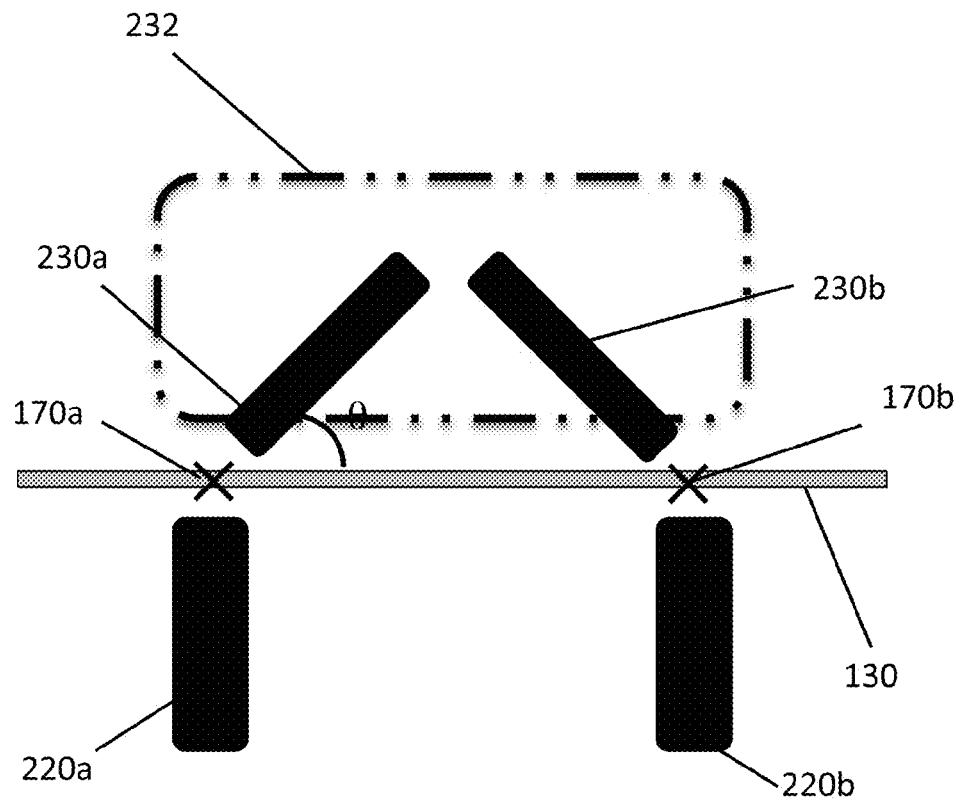

FIG. 14B is a schematic representation of a microfluidic system comprising two light devices and two light detection components, wherein the light detection components are mounted on a removable cartridge.

FIG. 15A, FIG. 15B, and FIG. 15C show calculations for Mie scattering.

Figure 16A:
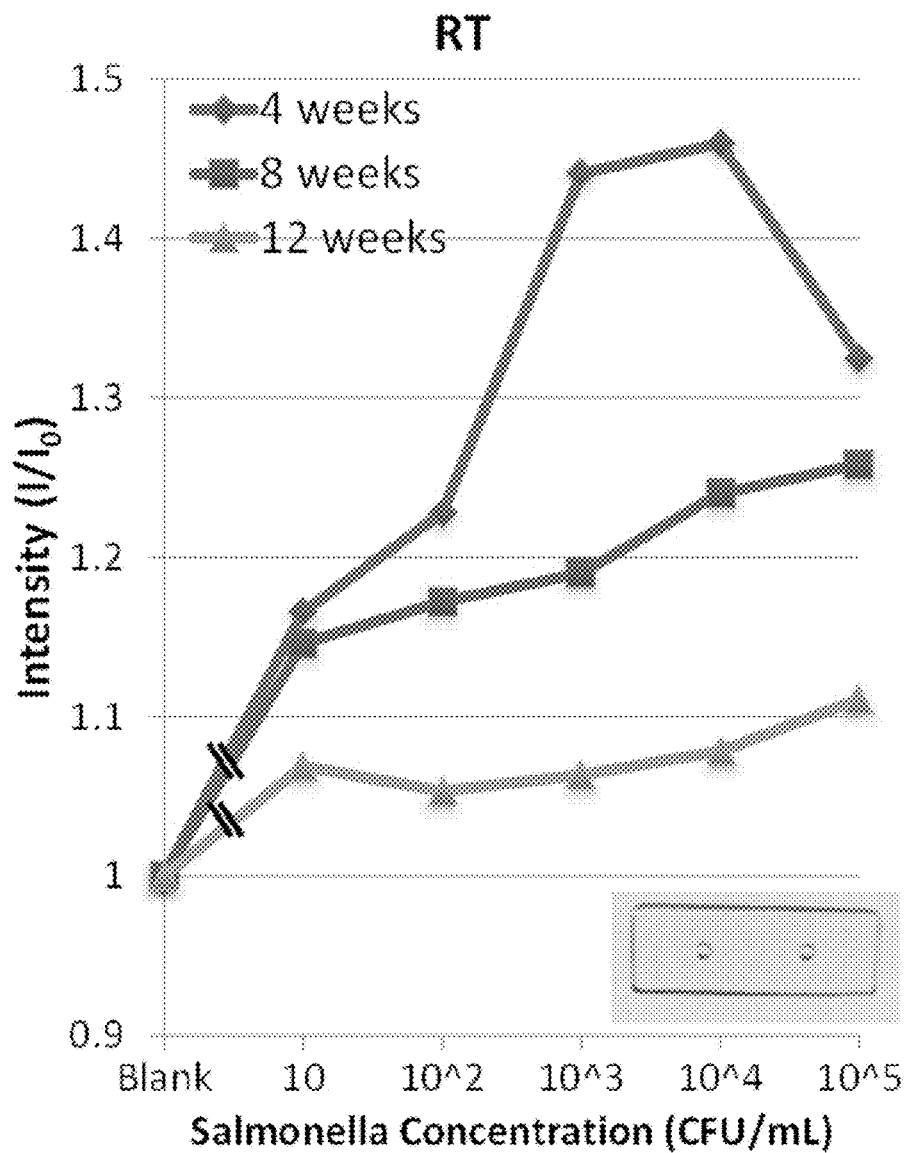
Figure 16B:
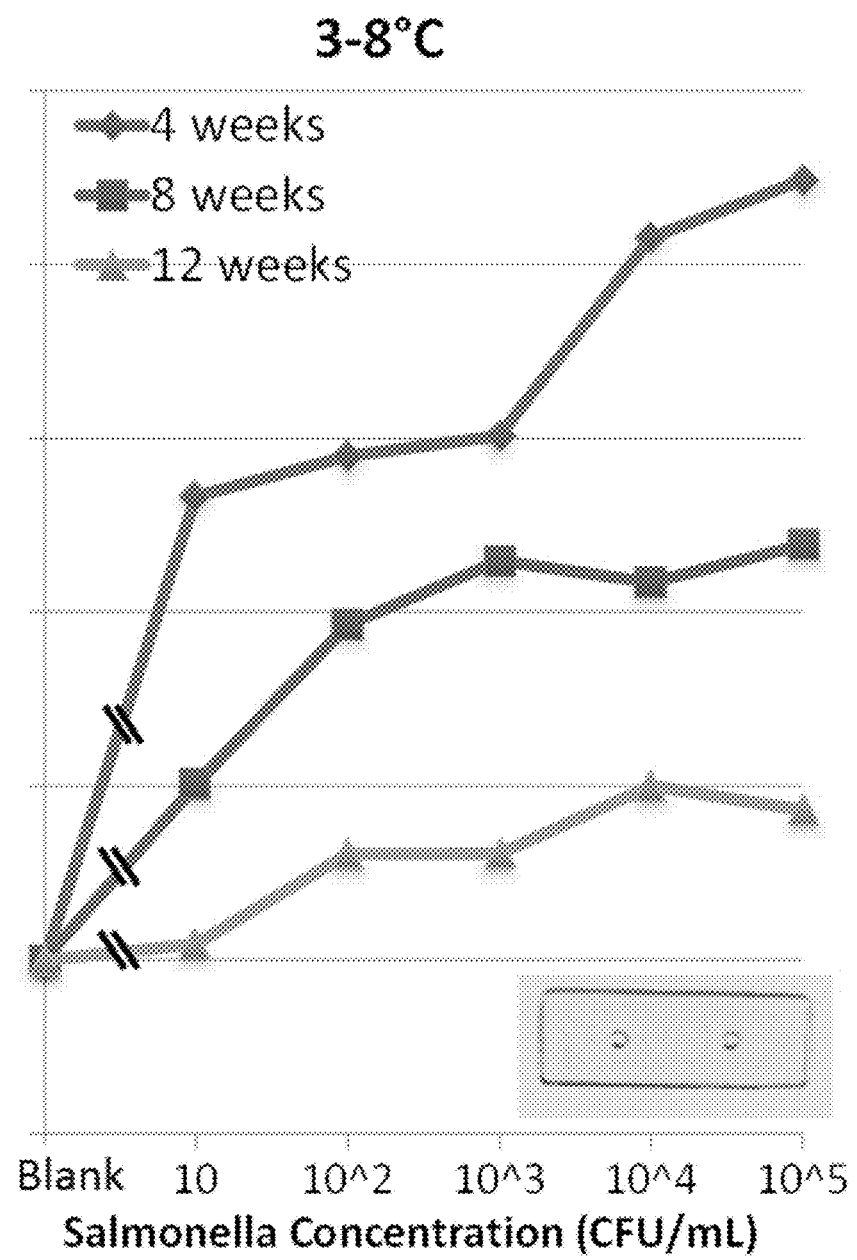
Figure 16C:
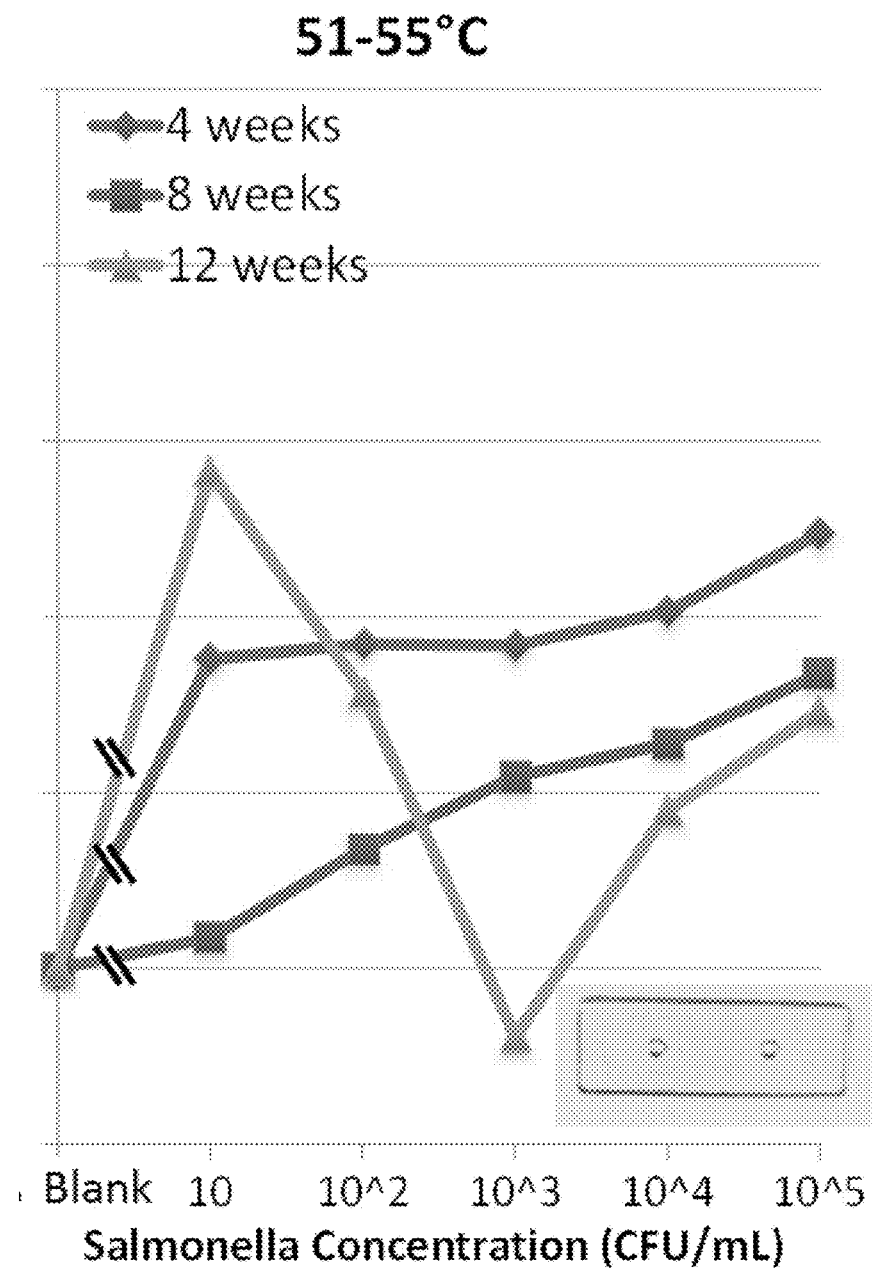

FIG. 16A, FIG. 16B, and FIG. 16C show a long-term storage study, e.g., normalized light scatter intensities against the *Salmonella* concentrations using the vacuum-dried particles stored for 4, 8 and 12 weeks in room temperature (RT), 3-8° C., and 51-55° C. Two-well chips and PBS matrix were used. Averages of three different experiments. Error bars are standard errors.

Figure 17A:
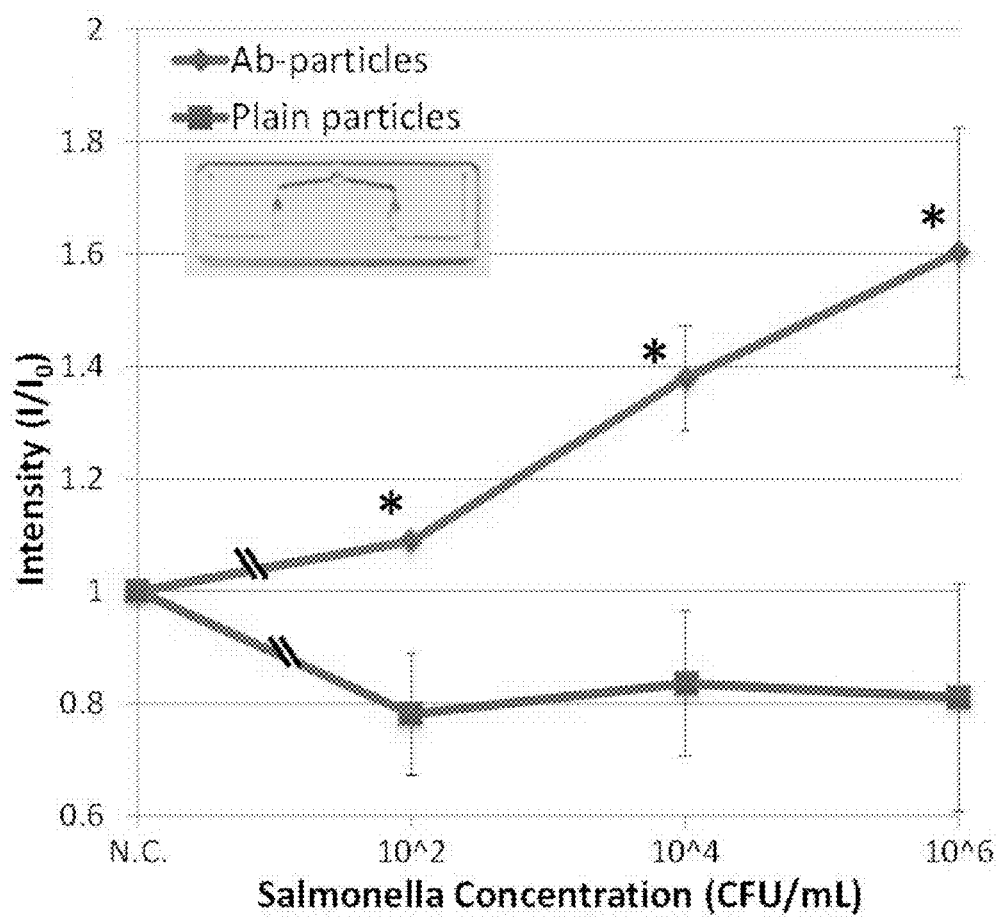

FIG. 17A shows normalized light scatter intensities against the *Salmonella* concentrations using the vacuum-dried particles in a microfluidic device and 1% chicken matrix. Both antibody-conjugated and plain (unconjugated) particles were used. Error bars are standard errors. Averages of three different experiments.

Figure 17B:
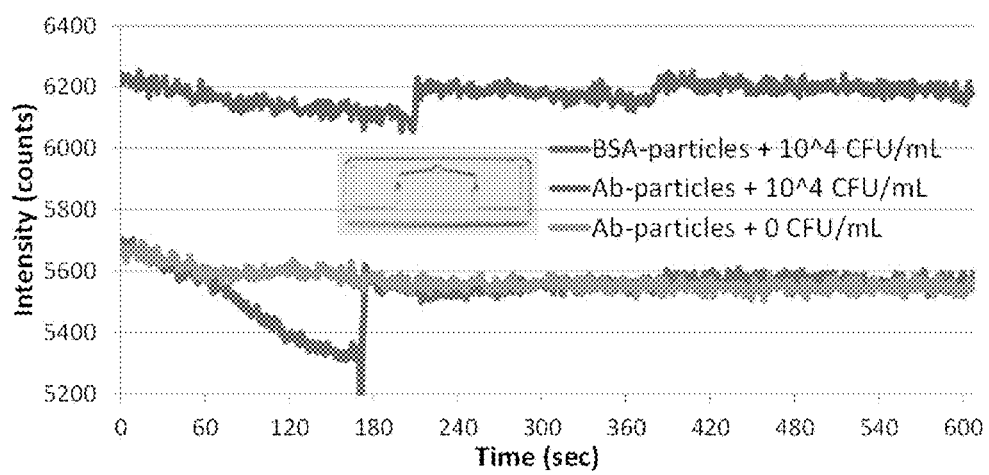

FIG. 17B shows real-time intensity changes for the select *Salmonella* concentrations and sample matrices, again using vacuum-dried particles, microfluidic device and 1% chicken matrix. BSA-conjugated particles were used instead of plain particles.

Figure 17C:
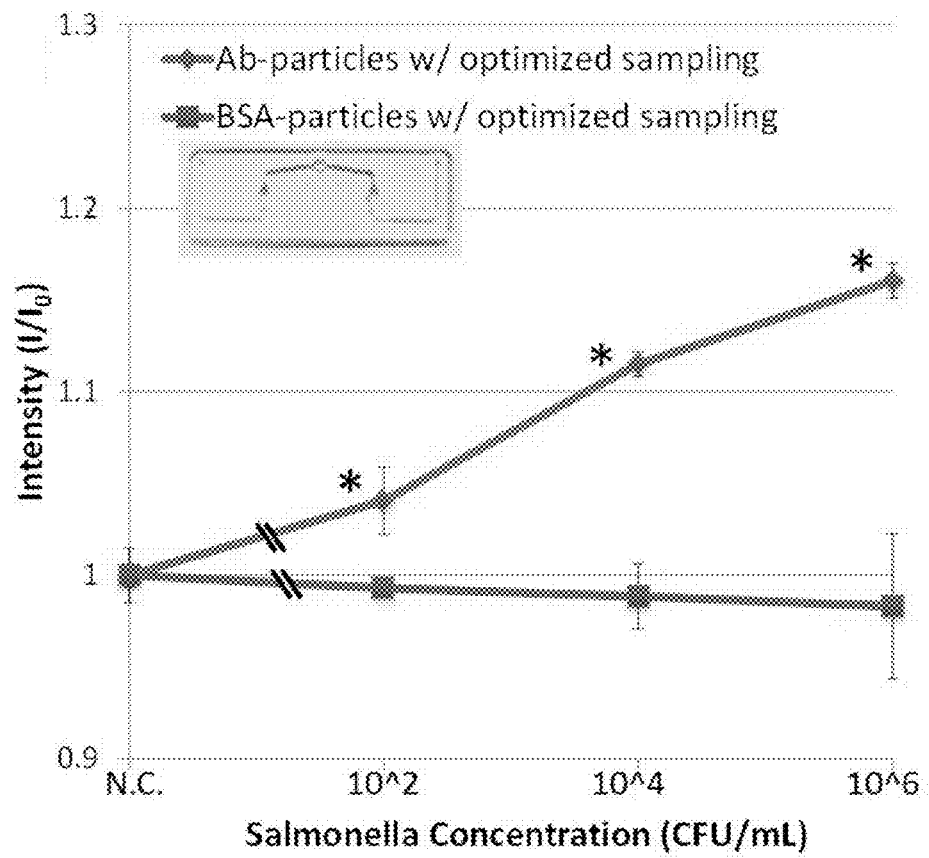

FIG. 17C shows a repeat of 17A but with BSA-conjugated particles and the optimized window of sampling time. Averages of three different experiments. Error bars are standard errors.

Figure 18:
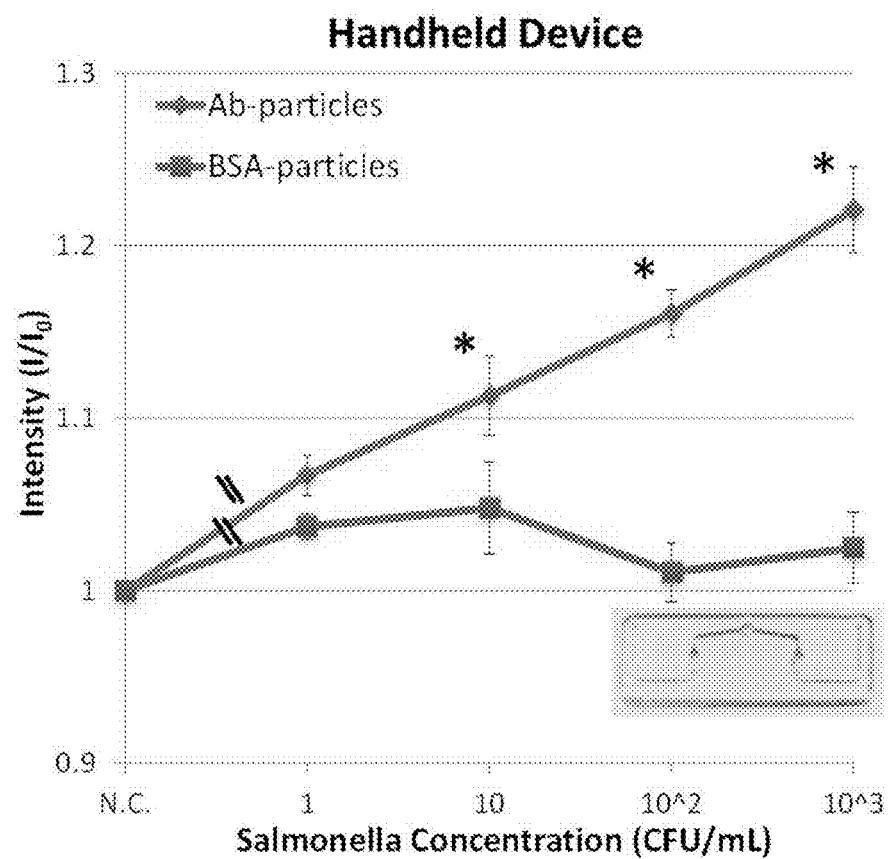

FIG. 18 shows assay results with handheld device, normalized light scatter intensities (normalized output voltages in mV scale) against the *Salmonella* concentration using the vacuum-dried particles (antibody- and 33%-BSA-), microfluidic device, 10% chicken matrix. Averages of three different experiments. Error bars are standard errors.

Figure 19:
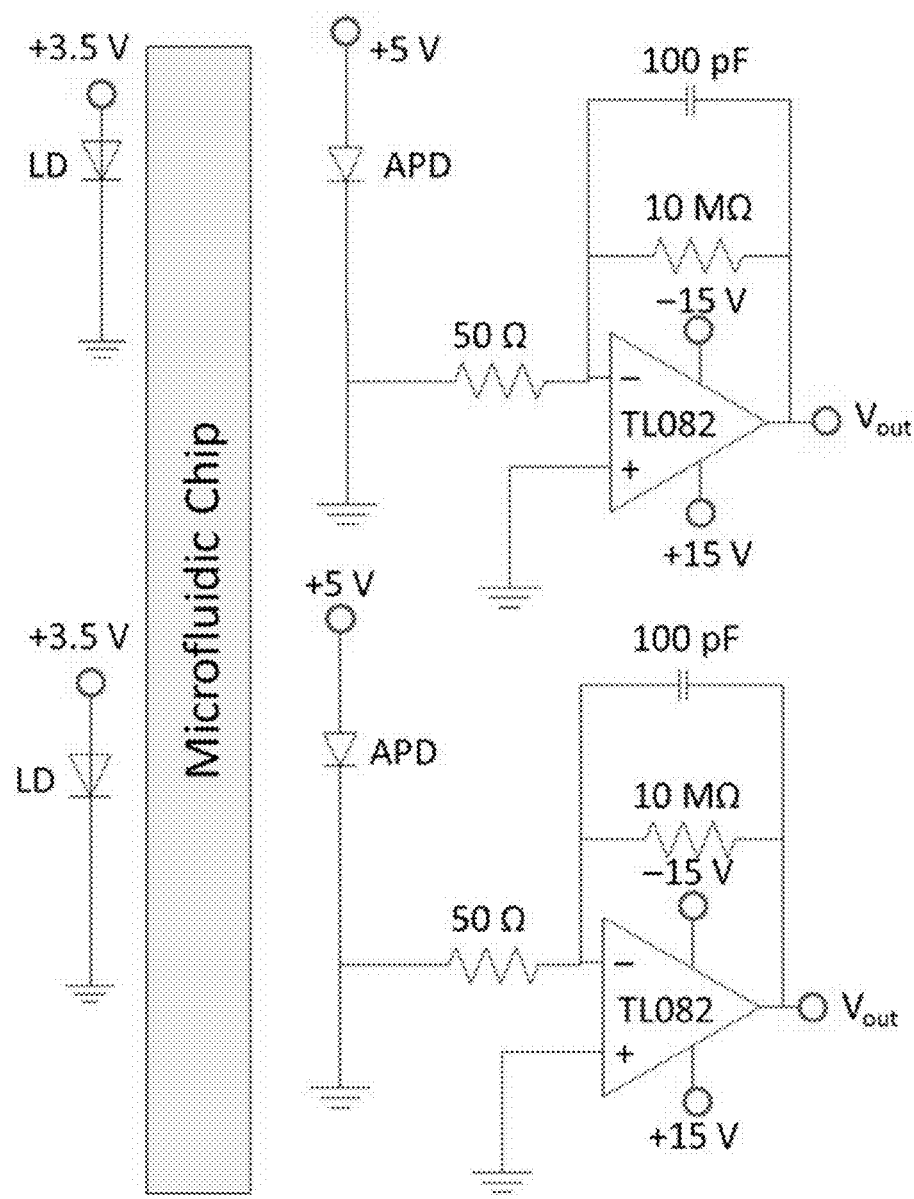

FIG. 19 shows a circuit diagram of a system of the present invention.

DESCRIPTION OF PREFERRED EMBODIMENTS

Referring now to FIG. 1-19, the present invention features microfluidic systems, methods, and devices (e.g., hand-held) for detecting microorganisms in samples (e.g., food/vegetable samples, fluid samples, etc.). Without wishing to limit the present invention to any theory or mechanism, it is believed that the system of the present invention is advantageous because it features the differential detection of positive and negative samples in a single assay. For example, a multi-channel design with parallel light sources and photodiodes, coupled with a differential op-amp circuit, allows for detection based predominantly on antibody-antigen bonding, and not residual plant cellular debris and other particulates present in the sample.

As used herein, the term "simultaneous" refers to the detection of two (or more) signals of scattered light (e.g., Mie scattering) from a single chip, as opposed to the detection of the signals at the exact same time. A single slide or chip is used and is not repositioned between readings. For example, no repositioning of the slide or chip occurs if the readings are done at different times.

In some embodiments, the microorganism is a bacterium, an archaea, a protist, a fungus, a microscopic plant, a microscopic animal, or a virus. Bacteria may include *Escherichia coli, Salmonella typhimurium, Acetobacter aurantius, Acinetobacter baumannii, Actinomyces Israelii, Agrobacterium radiobacter, Agrobacterium tumefaciens, Azorhizobium caulinodans, Azotobacter vinelandii, Anaplasma phagocytophilum, Anaplasma marginale, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides fragilis, Bacteroides gingivalis, Bacteroides melaninogenicus* (e.g., *Prevotella melaninogenica*), *Barto-* nella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae (e.g., *Chlamydia pneumoniae*), Chlamydophila psittaci (e.g., *Chlamydia psittaci*), Clostridium botulinum, Clostridium difficile, Clostridium perfringens (e.g., Clostridium welchii), Clostridium tetani, Corynebacterium diphtheriae, Corynebacterium fusiforme, Coxiella bumetii, Ehrlichia chaffeensis, Enterobacter cloacae, Enterococcus avium, Enterococcus durans, Enterococcus faecalis, Enterococcus faecium, Enterococcus galllinarum, Enterococcus maloratus, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Smreptococcus mutans, Streptococcus oralis, Stayyereyofhia mioms, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Yersinia enterocolitica, Yersinia pestis, Yersinia or pseudotuberculosis.

The *Escherichia coli* strain may include strain K12, P157:h7, P42, 101-1,1180, 1357, 1412, 1520, 1827-70, 2362-75, 3431, 53638, 83972, 929-78, 98NK2, ABU 83972, B, B088, B171, B185, B354, B646, B7A, C, c7122, CFT073, DH1, DH5[alpha], E210019, E128010, E74/68, E851171, EAEC 042, EPECa11, EPECa12, EPECa14, ETEC, H10407, F11, F18+, FVEC1302, FVEC1412, GEMS_EPEC1, HB101, HT115, K011, LF82, LT-41, LT-62, LT-68, MS 107-1, MS 119-7, MS 124-1, MS 145-7, MS 79-2, MS 85-1, NCTC 86, Nissle 1917, NT:H19, NT:H40, NU14, O103:H2, O103:HNM, O103:K+, O104:H12, O108:H25, O109:H9, O111:H−, O111:H19, O111:H2, O111:H21, O111:NM, O115:H−, O115:HMN, O115:K+, O119:H6, O119:UT, O124:H40, O127a:H6, O127:H6, O128:H2, O131:H25, O136:H−, O139:H28 (strain E24377A/ETEC), O13:H11, O142:H6, O145:H−, O153:H21, O153:H7, O154: H9, O157:12, O157:H−, O157:H12, O157:H43, O157:H45, O157:H7 EDL933, O157:NM, O15:NM, O177:H11, O17:K52:H18 (strain UMNO26/ExPEC), O180:H−, O1:K1/APEC, O26, O26:H−, O26:H11, O26:H11:K60, O26:NM, O41:H−, O45:K1 (strain S88/ExPEC), O51:H−, O55:H51, O55:H6, O55:H7, O5:H−, O6, O63:H6, O63:HNM, O6:K15:H31 (strain 536/UPEC), O7:K1 (strain IA139/ExPEC), O8 (strain IA11), O81 (strain ED1a), O84:H−, O86a:H34, O86a:H40, O90:H8, O91:H21, O9:H4 (strain HS), O9:H51, ONT:H−, ONT:H25, OP50, Orough:H12, Orough:H19, Orough:H34, Orough:H37, Orough:H9, OUT:H12, OUT:H45, OUT:H6, OUT:H7, OUT:HNM, OUT:NM, RN587/1, RS218, 55989/EAEC, B/BL21,B/BL21−DE3, SE11, SMS-3-5/SECEC, UTI89/UPEC, TA004, TA155, TX1999, Vir68.

Methods for Detecting Microorganisms

The present invention features systems and methods for detecting a microorganism and/or detecting a level of said microorganism.

In some embodiments, the method of the present invention comprises providing a first mixture, which comprises a first bead suspension. The beads in the first bead suspension are conjugated with an antibody specific for the microorganism (e.g., see FIG. 1). The first mixture further comprises a sample that is being tested for the presence (and/or for a level of) a microorganism. The first mixture is obtained by mixing the first bead suspension with a portion of the sample. The mixing of the sample and the bead suspension occurs via diffusional mixing, hence mechanical mixing (e.g., vibration, vortexing or shaking) is not required. This spontaneous mixing is made possible via use of highly carboxylated polystyrene beads. Generally, the microorganism may bind to the specific antibody, causing agglutination to occur (see FIG. 2).

In some embodiments, the method further comprises providing a second mixture (e.g., control mixture). In some embodiments, the second mixture comprises a second bead suspension with beads, wherein the beads in the second bead suspension are not conjugated with an antibody, and a portion of the sample. Like the first mixture, the mixing of the sample and the second bead suspension occurs via diffusional mixing. Generally, the microorganism in the sample does not cause agglutination to occur because the second mixture lacks antibody (e.g., antibody specific for the microorganism). In some embodiments, the second mixture comprises the sample alone (e.g., no second bead suspension). In some embodiments, the second mixture comprises the second bead suspension alone (e.g., no sample). In some embodiments, the second mixture comprises the beads alone (e.g., no sample, not antibodies). In some embodiments, the second mixture comprises the sample and antibody that is not bound to beads (e.g., no beads). Controls are well known to one of ordinary skill in the art.

In some embodiments, the method comprises providing a sample and introducing the sample to a test slide 130, wherein the sample diffuses through channels 140 in the test slide 130 and the first mixture and the second mixture are created when the sample flows through the channels 140. For example, in some embodiments, a test slide 130 comprises a first channel 140*a* with a first portion of lyophilized antibody-conjugated microparticles 144*a*. When the sample mixes with the first portion of lyophilized antibody-conjugated microparticles 144*a*, the first mixture is created. The test slide 130 is described in further detail below.

The method further comprises: (a) irradiating the first mixture with a light (e.g., a first incident light) and detecting a forward scattered light scattered by the first mixture, and (b) irradiating the second mixture with a light (e.g., a second incident light) and detecting a forward scattered light scattered by the second mixture when the mixtures are present on a single test slide 130, e.g., the irradiating of the mixtures and detecting of the scattered light occurs without repositioning of the test slide 130.

The forward scattered light is Mie scattering. Mie scattering equations have been described in: Kerker, 1969, The Scattering of Light and Other Electromagnetic Radiation, Academic Press, New York; van de Hulst, 1983, Light Scattering by Small Particles, John Wiley & Sons, New York; Bohren and Huffman, 1983, Absorption and Scattering of Light by Small Particles; and Cai et al., 2008, J. Quant. Spectrosc. Radiat. Transfer 109, 2673-2678. FIG. 15A shows the calculations of Mie scattering intensities wherein $i_1$ and $i_2$ are the complex scattering amplitudes for two orthogonal directions of incident polarization, n is the refractive index, and $\pi_n$ and $\tau_n$ are the angular dependent functions expressed in terms of Legendre polynomials. The scattering coefficients $a_n$ and $b_n$ are shown in FIG. 15B wherein $A_n$ and B are the quantities that depend on the ratios and logarithmic derivatives of the Riccati-Bessel functions, $\zeta_n$ and $\zeta_{\psi n}$ Riccati-Bessel functions are shown in FIG. 15C wherein $J_{n+1/2}(Z)$ is the half-interger-order Bessel function of the first kind, $Y_{n+1/2}(z)$ is the half-integer-order Bessel function of the second kind, and $z=\pi d/\lambda$, the size parameter of the scatterer. For Rayleigh scatter, wavelength is the dominant parameter; for Mie scatter, when the particle diameter is equal to or greater than the wavelength, the particle diameter is instead the dominant parameter. Therefore, the equations in FIGS. 15B and 15C indicate the Mie scatter intensity is dependent upon the particle size d and less dependent upon wavelength $\lambda$ compared to Rayleigh scatter. The equation in FIG. 15A also shows dependency on the scattering angle $\theta$.

The forward scattered light scattered by the first mixture that is detected is at a first angle ($\theta_1$) with respect to the light (e.g., first incident light). The forward scattered light scattered by the second mixture that is detected is at a second angle ($\theta_2$) with respect to the light (e.g., the second incident light), the second angle being the same as the first angle ($\theta_1=\theta_2$). The first angle ($\theta_1$) (and thus the second angle $\theta_2$) may be between about 30 to 60 degrees, e.g., about 30 degrees, about 31 degrees, about 32 degrees, about 33 degrees, about 34 degrees, about 35 degrees, about 36 degrees, about 37 degrees, about 38 degrees, about 39 degrees, about 40 degrees, about 41 degrees, about 42 degrees, about 43 degrees, about 44 degrees, about 45 degrees, about 46 degrees, about 47 degrees, about 48 degrees, about 49 degrees, about 50 degrees, about 51 degrees, about 52 degrees, about 53 degrees, about 54 degrees, about 55 degrees, about 56 degrees, about 57 degrees, about 58 degrees, about 59 degrees, about 60 degrees, etc. In some embodiments, the first angle may be between about 20 to 70 degrees. In some embodiments, the first angle may be between about 15 to 75 degrees.

The method further comprises determining I from the forward scattered light scattered by the first mixture, determining $I_0$ from the forward scattered light that is detected from the second mixture, and comparing I with $I_0$. Forward scattered light may be detected via a light detection component 230. In some embodiments, the measurements made by the light detection component 230 (e.g., voltage signals) are representative of I and $I_0$. For example, the actual light intensity is proportional to the voltage signal detected by the light detection component. Thus, the voltage signals can be treated as relative light intensity values (as opposed to actual light intensity values) and processed accordingly, e.g., in some embodiments, a ratio of $I/I_0$ is calculated, in some embodiments, a difference between I and $I_0$ is calculated (e.g., by subtracting of $I_0$ from of I), in some embodiments, $I/I_0$ is converted to an alternative representation number (e.g., a numerical representation of colony forming units (CFU) per ml, a numerical representation of CFU per gram, etc.). In some embodiments, a ratio of $I/I_0$ that is greater than 1 indicates the presence of the microorganism in the sample. In some embodiments, a difference of greater than 0 indicates the presence of the microorganism in the sample. In some embodiments, the operational amplifier amplifies voltage outputs from the light detection component(s) (e.g., photodiode).

Microfluidic Device

The methods of the present invention comprise utilizing a microfluidic system 100 (e.g., device) as described herein. The microfluidic system 100 may be a small-scale hand-held system that allows the simultaneous (e.g., on the same test slide 130) irradiating of both the first mixture and the second mixture as previously described.

Figure 3:
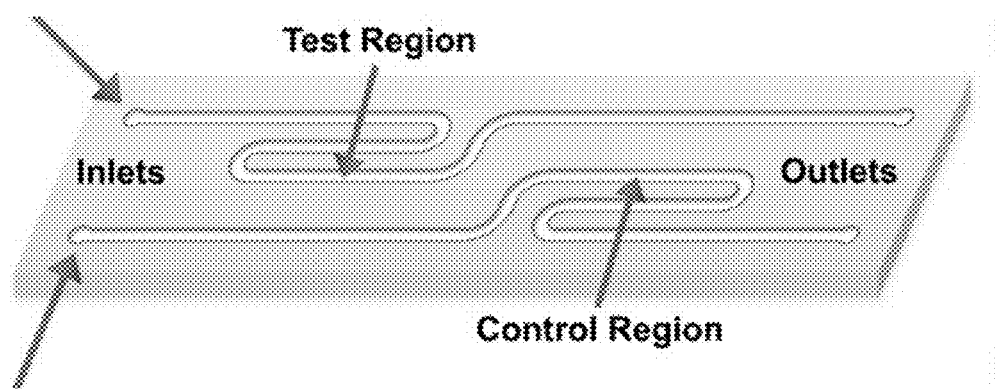

As shown in FIG. 3 and FIG. 5, the system 100 comprises a housing 110. Disposed in the housing 110 is a testing cavity 120 (e.g., see FIG. 5C), wherein the irradiation of the mixtures takes place and the Mie scattering is detected. In some embodiments, the testing cavity 120 is optically isolated from the remainder of the housing 110. In some embodiments, the testing cavity 120 is thermally isolated from the remainder of the housing 110.

The system 100 comprises a test slide 130 insertable into the testing cavity 120 of the housing 110. To irradiate the mixtures with the incident lights, the mixtures are inserted (e.g., via syringes) into the test slide 130 (e.g. see FIG. 3, see FIG. 10). The test slide 130 may have a variety of configurations (e.g., see TEST SLIDE below). Briefly, the test slide 130 comprises test regions 170, which are the portions of the channels 140 where the incident light hits the mixtures. For example, in some embodiments, each test slide 130 has a first testing region 170a for irradiating the first mixture (and detecting scattered light from the first mixture) and a second testing region 170b for irradiating the second mixture (and detecting scattered light from the second mixture).

In some embodiments, the test slide 130 is mounted atop a tray 180 disposed in the testing cavity. In some embodiments, the tray 180 can slide inwardly into and outwardly from the testing cavity of the housing 110 moving between a first position (e.g., see FIG. 5C) and a second position (e.g., see FIG. 5D). In some embodiments, the tray 180 temporarily locks into place when in the first position.

Test Slide

As shown in FIG. 3 and FIG. 10, the test slide 130 has a multi-channel configuration. For example, the test slide 130 comprises a first channel 140a and a second channel 140b. The channels 140 extend through a portion of the test slide 130. Each channel 140 has a first end and a second end. A first test region 170a is disposed in the first channel 140a, and a second test region 170b is disposed in the second channel 140b. The test regions 170 are the portions of the channels 140 where the incident light hits the mixtures.

As shown in FIG. 3, in some embodiments, the first end of the first channel 140a comprises a first inlet 150a (e.g., an opening), the second end of the first channel 140a comprises an outlet 160, the first end of the second channel 140b comprises a second inlet 150b that is separate from the first inlet 150a of the first channel 140a, and the second end of the second channel 140b comprises an outlet 160. In some embodiments, the first mixture is added to the first inlet 150*a* and travels through the first channel 140*a* towards the first outlet 160*a*. In some embodiments, the second mixture is added to the second inlet 150*b* and travels through the second channel 140*b* towards the second outlet 160*b*.

As shown in FIG. 10, in some embodiments, the test slide 130 comprises two channels 140 each with a first end and a second end, wherein the first ends of the channels 140 are joined together at an inlet 150 (e.g., the channels 140 share the inlet 150). In some embodiments, a first lyophilized portion of microparticles 144*a* is disposed in the first channel 140*a*. The first lyophilized portion of microparticles 144*a* comprises a lyophilized portion of antibody-conjugated microparticles. In some embodiments, a portion of detergent 146 (e.g., polysorbate detergent, e.g., Tween, e.g., Tween-80) is disposed in the first channel 140*a*, wherein the portion of detergent 146 is positioned closer to the inlet 150 than is the first lyophilized portion of microparticles 144*a* such that the sample that is inserted into the inlet 150 mixes with the portion of the detergent 146 prior to reaching the first lyophilized portion of microparticles 144*a*. In some embodiments, a second lyophilized portion of microparticles 144*b* is disposed in the second channel 140*b*. In some embodiments, the second lyophilized portion of microparticles 144*b* comprises a lyophilized portion of microparticles that are not conjugated with an antibody. The second lyophilized portion of microparticles 144*b* is not limited to this composition; the second lyophilized portion of microparticles 144*b* may comprise any appropriate reagent for a control (e.g., antibody alone, beads alone, no beads nor antibody, etc.). In some embodiments, a portion of detergent 146 (e.g., polysorbate detergent, e.g., Tween, e.g., Tween-80) is disposed in the second channel 140*b*, wherein the portion of detergent 146 is positioned closer to the inlet 150 than is the second lyophilized portion of microparticles 144*b* such that the sample that is inserted into the inlet 150 mixes with the portion of the detergent 146 prior to reaching the second lyophilized portion of microparticles 144*b*. In some embodiments, when the sample is added to the inlet 150 (e.g., via a syringe), the sample splits and a portion travels through the first channel 140*a* and a portion travels through the second channel 140*b*. In some embodiments, the portion of the sample interacts with its respective portion of detergent 146. In some embodiments, the portion of the sample interacts with its respective lyophilized portion of microparticles 144 and then travels to its respective test region 170. In some embodiments, a viewing chamber 149 is disposed in the channels 140 (e.g., see FIG. 10).

In some embodiments, e.g., using the test slide 130 shown in FIG. 3, a user may allow between about 30 to 45 seconds for diffusion of the sample. In some embodiments, e.g., using the test slide 130 shown in FIG. 3, a user may allow between about 45 to 60 seconds for diffusion of the sample. In some embodiments, e.g., using the test slide 130 shown in FIG. 3, a user may allow between about 60 to 120 seconds for diffusion of the sample. In some embodiments, e.g., using the test slide 130 shown in FIG. 3, a user may allow more than about 120 seconds for diffusion of the sample.

In some embodiments, e.g., using the test slide 130 shown in FIG. 10, a user may allow between about 1 to 10 minutes for diffusion of the sample. In some embodiments, e.g., using the test slide 130 shown in FIG. 10, a user may allow between about 2 to 10 minutes for diffusion of the sample. In some embodiments, e.g., using the test slide 130 shown in FIG. 10, a user may allow between about 3 to 10 minutes for diffusion of the sample. In some embodiments, e.g., using the test slide 130 shown in FIG. 10, a user may allow between about 4 to 10 minutes for diffusion of the sample. In some embodiments, e.g., using the test slide 130 shown in FIG. 10, a user may allow between about 5 to 10 minutes for diffusion of the sample. In some embodiments, e.g., using the test slide 130 shown in FIG. 10, a user may allow more than about 10 minutes for diffusion of the sample.

The test slide 130 may be constructed using standard photolithography methods, which are well known to one of ordinary skill in the art (e.g., see Heinze et al., 2010, Anal. Bioanal. Chem. 398, 2693-2700). The test slide 130 may be constructed from a variety of materials (e.g., a material comprising polydimethylsiloxane (PDMS), a material comprising glass, etc.) and in a variety of sizes (e.g., the size of a standard microscope slide). In some embodiments, the channels 140 are between about 0.5 and 1.0 mm in width. In some embodiments, the channels 140 are between about 0.25 and 0.5 mm in width. In some embodiments, the channels 140 are between about 0.5 and 1.5 mm in width. In some embodiments, the channels 140 are between about 20 and 80 μm in depth. In some embodiments, the channels 140 are between about 60 and 100 μm in depth. In some embodiments, the channels 140 are between about 80 and 120 μm in depth. In some embodiments, the channels 140 are between about 10 and 50 μm in depth. In some embodiments, the channels 140 are between about 50 and 150 μm in depth. The channels 140 are not limited to the aforementioned dimensions. The test slide 130 is not limited to the aforementioned dimensions and materials.

Light Device

The system 100 of the present invention comprises a light device 220, e.g., a single light device 220, a first light device 220*a* and a second light device 220*b*, etc., that produces light (e.g., first incident light, the second incident light) to irradiate the mixtures as previously described.

In some embodiments, the light (e.g., first incident light, second incident light) has a wavelength ($\lambda$) between about 320 to 800 nm. In some embodiments, the light (e.g., first incident light, second incident light) has a wavelength ($\lambda$) of about 375 nm. In some embodiments, the light (e.g., first incident light, second incident light) has a wavelength ($\lambda$) of about 650 nm. In some embodiments, the light has a wavelength ($\lambda$) of about 470 nm. In some embodiments, a wavelength significantly smaller than the particle size (e.g., diameter) may be selected to induce Mie light scattering, which depends primarily on the particle size. In some embodiments, an ultraviolet wavelength is used, for example, because of the energy it provides. Without wishing to limit the present invention to any theory or mechanism, it is believed that in some cases ultraviolet wavelengths may be advantageous because they have more energy and thus may penetrate a sample more efficiently.

In some embodiments, the light device 220 comprises a light emitting diode (LED) (e.g., continuous LED), a laser diode (e.g., 3.3 mm laser diode), or the like. In some embodiments, the light device 220 comprises laser diode modules (e.g., Lasers4U, Walnut Creek, Calif.) and collimating lenses (e.g., acrylic, aspheric collimating lenses, Lasers4U, Walnut Creek, Calif.). For example, in some embodiments, the first light device 220*a* comprises a first laser diode (e.g., 3.3 mm) and a first collimating lens (e.g., 7 mm), and the second light comprises 220*b* a second laser diode (e.g., 3.3 mm) and a second collimating lens (e.g., 7 mm). The laser diodes and collimating lenses are not limited to the aforementioned dimensions. In some embodiments, the laser diode intensities are calibrated, e.g., using a spectrometer, e.g., a USB4000 miniature spectrometer (Ocean Optics, Inc., Dunedin, Fla.). In some embodiments, power to the laser diode modules is simultaneously moderated by a LTC1477 digital switch (Sparkfun Electronics) controlled by the processing system, e.g., microprocessor. In some embodiments, the intensity of each laser module is independently adjusted by a 10 kΩ potentiometer.

In some embodiments, the light (λ) from the light device 220 is transmitted via a light conduit 228, e.g., fiber optics, light pipe, etc. Fiber optics and light pipes are well known to one of ordinary skill in the art. For example, as shown in FIG. 12, in some embodiments, a single light device 220 is used to generate both the first incident light and the second incident light. A first beam splitter 226a (operatively connected to the light device 220) splits the light (2) of the light device 220 and transmits a first incident light to the first test region 170a of the test slide 130 (via a first arm 228a of the light conduit 228) and a second incident light to the second test region 170b of the test slide 130 (via the second arm 228b of the light conduit 228).

In some embodiments, as shown in FIG. 13, a first light device 220a transmits the first incident light of the first test region 170a of the test slide 130 and a second light device 220b transmits the second incident light to the second test region 170b of the test slide 130.

In some embodiments, the light (e.g., first incident light, second incident light) has an intensity of less than about 100 ρW. In some embodiments, the light (e.g., first incident light, second incident light) has an intensity of about 45 µW.

All or a portion of the light device 220 may be enclosed in the testing cavity 120 of the housing 110.

In some embodiments, the configuration of the light device 220, light conduits 228, light devices 220a, 220b results in a front focal point of about 5 mm. In some embodiments, the configuration of the light device 220, light conduits 228, light devices 220a, 220b results in a front focal point of between about 1 to 5 mm. In some embodiments, the configuration of the light device 220, light conduits 228, light devices 220a, 220b results in a front focal point of between about 2 to 8 mm. In some embodiments, the configuration of the light device 220, light conduits 228, light devices 220a, 220b results in a front focal point of between about 5 to 10 mm. The present invention is not limited to the aforementioned focal points.

Light Scattering Detection

Immunoagglutination in the mixtures (e.g., in the first mixture) may cause Mie scattering of incident light. Mie scattering refers to a solution of Maxwell's equations for the scattering of electromagnetic radiation by spherical particles. Mie scattering predominates at d≥λ (thus shorter wavelength, e.g., ultraviolet, may be preferred for submicron beads). Mie scattering is generally dependent on the size of the particle. The highest amount of scatter is generally at 0 degrees (θ=0) from the incident light; however, typically one cannot differentiate incident from scatter at 0 degrees. In some embodiments, an alternate angle to detect scattered light is about 45 degrees from the incident light (A=45), or between about 30 to 60 degrees (θ=between 30 to 60). Alternative angles (θ) are described below.

The forward light scattering by the first mixture that is detected is at a first angle ($\theta_1$) with respect to the light (λ) (e.g., first incident light). The forward light scattering by the second mixture that is detected is at a second angle ($\theta_2$) with respect to the light (λ) (e.g., second incident light), wherein the second angle is the same as the first angle ($\lambda_1=\theta_2$). As previously described, in some embodiments, the first angle ($\theta_1$) (and thus the second angle $\theta_2$) is a particular angle that may be between about 30 to 60 degrees, between about 20 to 70 degrees, between about 15 to 75 degrees, etc. As used herein, the term "about" refers to plus or minus 5% of the referenced number. For example, an embodiment wherein the first angle ($\theta_1$) is about 45 degrees includes a first angle ($\theta_1$) that is between 42.75 and 47.25 degrees.

The system 100 comprises a light detection component 230, or more than one light detection component 230 (e.g., a first light detection component 230a and a second light detection component 230b), for detecting the scattered light (Mie scattering from the mixtures). In some embodiments, as shown in FIG. 13, a first light detection component 230a (e.g., a first APD) detects scattered light by the first mixture, and a second light detection component 230b (e.g., a second APD) detects scattered light by the second mixture. In some embodiments, as shown in FIG. 12, a single light detection component 230 detects scattered light from both the first mixture and the second mixture. For example, a first arm 328a of a light conduit 328 transmits the scattered light (at the first angle) from the first mixture, and a second arm 328b of the light conduit 328 transmits the scattered light (at the second angle) from the second mixture. The light conduit 238 transmits the scattered light to the light detection component 230, e.g., via a second beam splitter 226b.

In some embodiments, the light detection component 230 comprises a photodiode, for example an avalanche photodiode (APD). APDs are well known to one of ordinary skill in the art (Barrington, N.J.). In some embodiments, the APD is a UV-visible light capable APD, e.g., the APD can detect a wavelength in the UV or visible spectrum.

The light detection component 230 (or each light detection component 230) has an active area. In some embodiments, the active area is between about 0.5 to 1.0 mm in diameter. In some embodiments, the active area is between about 0.25 to 1.0 mm in diameter. In some embodiments, the active area is between about 0.1 to 1.0 mm in diameter. In some embodiments, the active area is between about 0.5 to 2.0 mm in diameter. In some embodiments, the active area is about 1.0 mm in diameter.

All or a portion of the light detection component 230 may be enclosed in the testing cavity 120 of the housing 110.

The light detection component 230, or light detection components 230, are positioned at angles ($\theta_1$, $\theta_2$) with respect to the plane of the mixtures (e.g., the test slide 130, e.g., test regions 170 of the channels 140 of the test slide 130) so that the first light detection component 230a (e.g., first APD) detects scattered light from the first mixture at the first angle ($\theta_1$) and the second light detection component 230b (e.g., second APD) detects scattered light from the second mixture at the second angle ($\theta_2$) (the first angle $\theta_1$ and second angle $\theta_2$ being the same).

As previously discussed, in some embodiments, the light detection components 230 are mounted at a particular angle (e.g., 45 degrees, 46 degrees, 30 degrees, 60 degrees, 31 degrees, 35 degrees, 40 degrees, 50 degrees, 55 degrees, etc.) with respect to the plane of the mixtures (e.g., test slide 130, test regions 170). In some embodiments, the light detection components 230 are mounted at a fixed angle, e.g., the light detection component(s) 230 cannot be moved to detect an angle of choice, e.g., the light detection component(s) are fixed at the particular angle (e.g., 45 degrees, 46 degrees, 30 degrees, 60 degrees, 31 degrees, 35 degrees, 40 degrees, 50 degrees, 55 degrees, etc.) with respect to the plane of the mixtures (e.g., test slide 130, test regions 170).

In some embodiments, the light detection components 230 are removable from the housing 110. For example, as shown in FIG. 14B, in some embodiments, the light detection components 230 are fixedly mounted in cartridges 232 (at a particular angle), and the cartridges 232 can be removed from the housing 110. This can allow for a single housing 110 to be used with fixedly mounted light detection components 230 of different angles, e.g., the cartridges 232 are interchangeable within the housing 110. For example, a first cartridge 232 may comprise light detection components 230 at a first angle, e.g., 46 degrees, and a second cartridge may comprise light detection components 230 at a different angle, e.g., 50 degrees, and a third cartridge may comprise light detection components 230 at a different angle, e.g., 40 degrees, etc. In some embodiments, the cartridge holds the light detection component 230. In some embodiments, as shown in FIG. 14A, the cartridge 232 holds the arms 328a, 328b of the light conduit 328. In some embodiments, the cartridge 232 holds the second beam splitter. In some embodiments, the cartridge 232 holds the second beam splitter and the light detection component 230. The cartridges are not limited to the aforementioned configuration.

Processing System

The system 100 of the present invention comprises a processor system (e.g., microprocessor and optionally other components) operatively connected to the light device 220 and the light detection component 230. The processor system (e.g., microprocessor and optionally other components) controls the light device 220 and processes signals obtained from the light detection component 230. Processors and processor systems are well known to one of ordinary skill in the art.

The processor system comprises a microprocessor and may comprise a variety of additional components, e.g., a differential operational amplifier circuit, an analog-to-digital converter, the like, or a combination thereof. For example, in some embodiments, the processor system comprises an operational amplifier (op-amp) circuit (or multiple op-amp circuits) configured to amplify the signals (e.g., differential voltage signals) produced by the light detection component(s) 230. Op-amps are well known to one of ordinary skill in the art. In some embodiments, the processor system comprises an analog-to-digital converter (ADC) (e.g., a 24-bit ADC) operatively connected to the op-amp circuit for processing the signals. In some embodiments, the signals are statistically analyzed by software.

In some embodiments, the op-amps are configured to generate the I value from the first input signal from the light detection component 230 (or the first light detection component 230a) and the $I_0$ value from the second input signal from the light detection component 230 (or the second light detection component 230b). In some embodiments, the op-amps are configured to calculate a ratio of $I/I_0$ or a difference between I and $I_0$. In some embodiments, the op-amps comprise or are operatively connected to an analog-digital converter (ADC), wherein the analog-digital converter (ADC) converts an analog input from the operational amplifier circuit to a digital signal. In some embodiments, the digital signal is sent to the display 190 (e.g., via the microprocessor).

In some embodiments, the operational amplifier is a quadruple op-amp LM324. In some embodiments, the microprocessor is an Arduino Duemilanove microcontroller (Sparkfun Electronics). Arduino Duemilanove microcontrollers are well known to one of ordinary skill in the art.

In some embodiments, the processing system (e.g., microprocessor) is operatively connected to the light device 220. In some embodiments, the processing system (e.g., microprocessor) is operatively connected to the first light device 220a and the second light device 220b. In some embodiments, the processing system (e.g., microprocessor) is operatively connected to the light detection component 230.

In some embodiments, the processing system (e.g., microprocessor) is operatively connected to the first light detection component 230a and the second light detection component 230b.

In some embodiments, the processing system (e.g., microprocessor) is configured to calculate an I value from a first input signal from the light detection component 230 and an $I_0$ value from a second input signal from the light detection component 230. In some embodiments, the processing system (e.g., microprocessor) is configured to calculate an I value from a first input signal from the first light detection component 230a and an $I_0$ value from a second input signal from the second light detection component 230b. The input signals are converted to processed signals (e.g., I and $I_0$ and/or the ratio of $I/I_0$ and/or the difference between I and $I_0$, and/or a CFU/ml unit or the like).

In some embodiments, the microprocessor is configured to calculate a ratio of $I/I_0$ or a difference between I and $I_0$, or the like. In some embodiments, the system 100 of the present invention comprises a display component 190 (e.g., a liquid crystal display (LCD) display) for displaying the processed signals, e.g., I and $I_0$ and/or the ratio of $I/I_0$ and/or the difference between I and $I_0$, and/or a CFU/ml unit or the like.

The system 100 of the present invention comprises a power source. The power source may be operatively connected to the light device 220, the light detection component 230, the display component 190, and/or the microprocessor and/or other components of the processing system. In some embodiments, the power source is a battery. In some embodiments, the battery is a 9 volt battery. In some embodiments, the battery is a lithium ion rechargeable battery.

In some embodiments, the system 100 of the present invention further comprises a USB interface for either programming or retrieving data. USB interfaces are well known to one of ordinary skill in the art. In some embodiments, the USB interface is used to retrieve data from previous assays (e.g., stored data).

Antibody-Conjugated Beads

The beads (e.g., microspheres) in the first bead suspension and/or the second bead suspension may be constructed in a variety of sizes and from a variety of materials. For example, in some embodiments, the beads have a diameter between about 200 to 1,000 nm. In some embodiments, the beads have a diameter of about 920 nm. In some embodiments, the beads are constructed from a material comprising a hydrophobic material (e.g., a hydrophobic core), for example a material comprising polystyrene (e.g., a polystyrene core). In some embodiments, the beads are constructed from a material comprising a hydrophilic material (e.g., a hydrophilic outer surface), for example a material comprising one or more carboxyl groups (e.g., a plurality of carboxyl groups disposed on an outer surface). The beads, for example the outer surfaces of the beads, may comprise at least 5 carboxyl groups per $nm^2$ surface area. The carboxyl groups may include but are not limited to polyacrylic acid (PAA) or polymethacrylic acid (PMAA). Beads may be obtained, for example, from Bangs Laboratories, Fishers, Ind.

Figure 1:
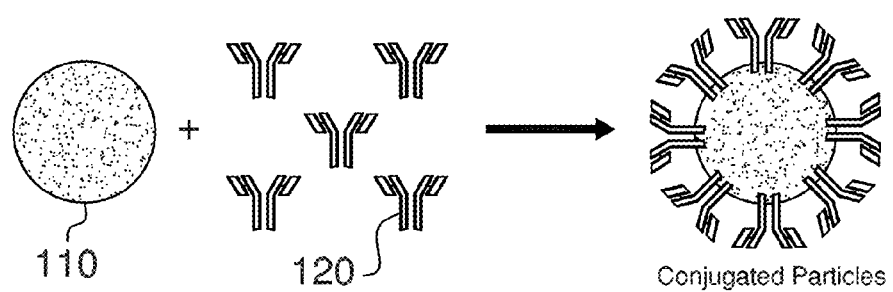
Figure 2:
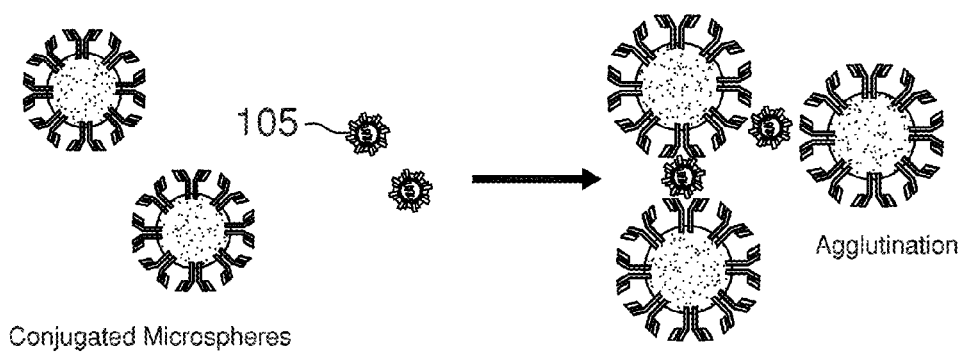

The beads in the first bead suspension are conjugated with an antibody specific for the microorganism (see FIG. 1). Antibody conjugation can occur either via passive adsorption or covalent binding, although in some examples, covalent binding may be preferred. These protocols are available in public domain. In some embodiments, the antibody is a monoclonal or a polyclonal antibody.

Sample Preparation

Samples, for example food samples (e.g., vegetable samples), may be prepared in a variety of ways. A vegetable sample may be chopped up and added to a buffer, for example, at a ratio of about 1:1 to 1:3 (vegetable to buffer). The sample may be further diluted as needed. In some embodiments, the sample is then filtered with a common cloth or tissue component (e.g., KimWipes, Kimberly-Clark Corporation). Without wishing to limit the present invention to any theory or mechanism, the process of filtering the sample with a tissue component is advantageous because it helps to quickly and easily remove large chunks or particles in the sample. This may be faster (and possibly cheaper) than if a filtration apparatus or procedures are used (e.g., centrifugation, etc.). A cloth or tissue component or other filtering component may not be necessary in some instances. In some embodiments, a sample is prepared by washing a food and using the wash solution as the sample. Bacteria on the outer surface of the food would be harvested by such washing.

In some embodiments, a syringe is pre-filled with a dilution solution, e.g., PBS, to a certain volume, e.g., 90 ml. The syringe can then be used to suck in a volume of sample so as to dilute the sample. For example, in some embodiments, the syringe comprises a 90 ml dilution solution and 10 ml of sample is sucked into the syringe, creating a 1:10 dilution of the sample.

System Customization

Each sample, e.g., sample matrix (whole food, ground food, filtered food), particle, etc., has a different Mie light scattering curve at a particular light wavelength, $\lambda$ based on its refractive index, n as well as other parameters such as particle size d and concentration of particles, etc. Generally, at least one peak (e.g., a "maximum light scattering intensity") is detected at a particular forward scattering angle $\theta$ (e.g., a "maximum scattering angle").

Figure 4:
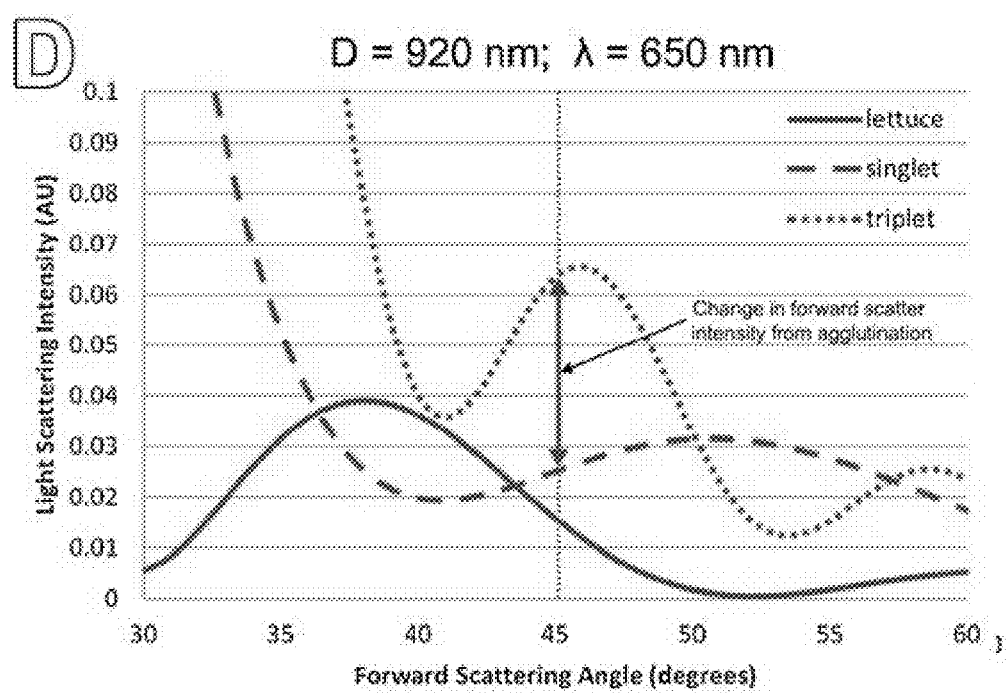
Figure 5A:
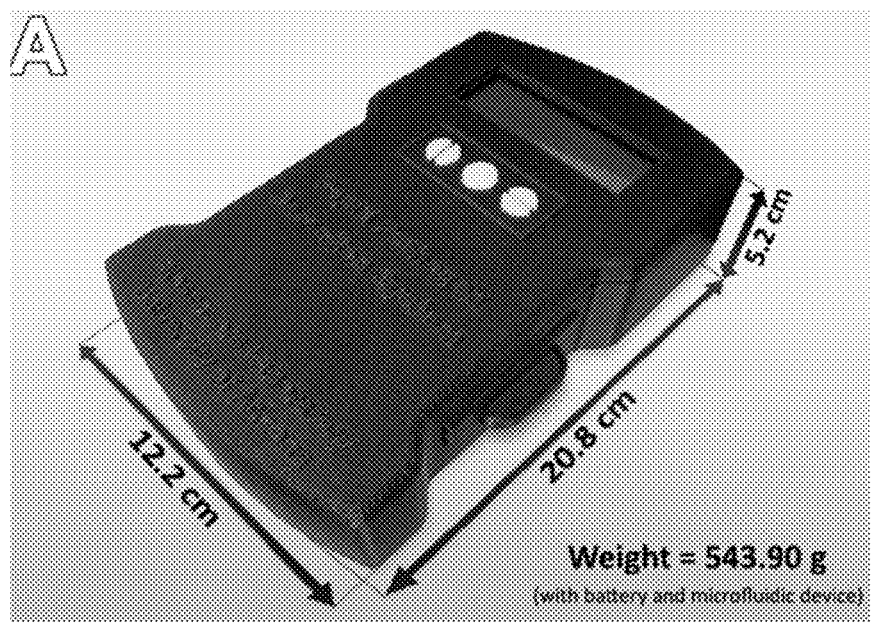
FIG. 5D is a detailed view of the tray and test slide of the system of FIG. 5A.
Figure 5B:
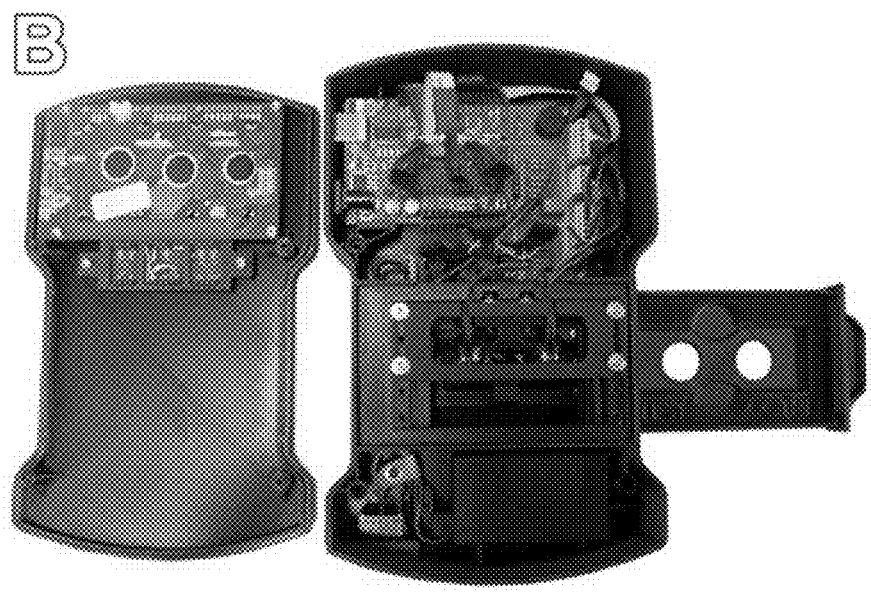
Figure 5C:
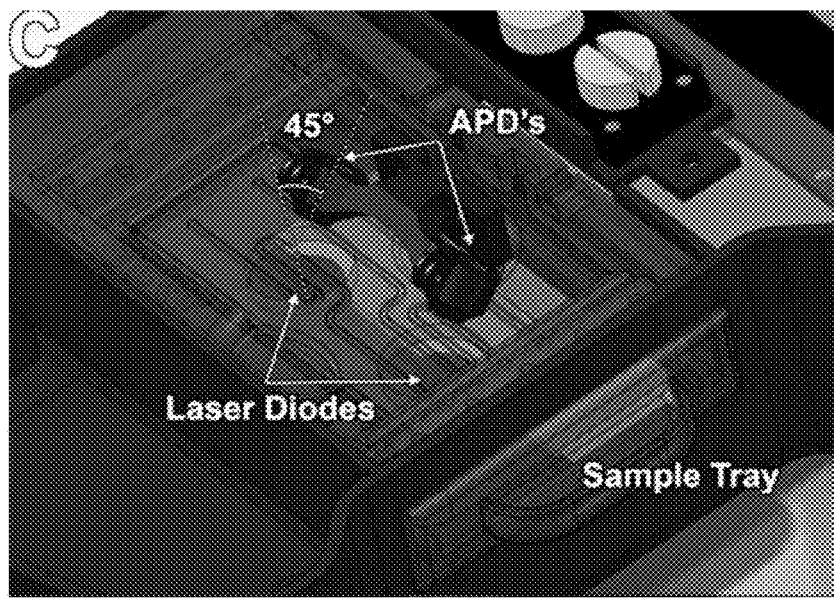
Figure 5D:
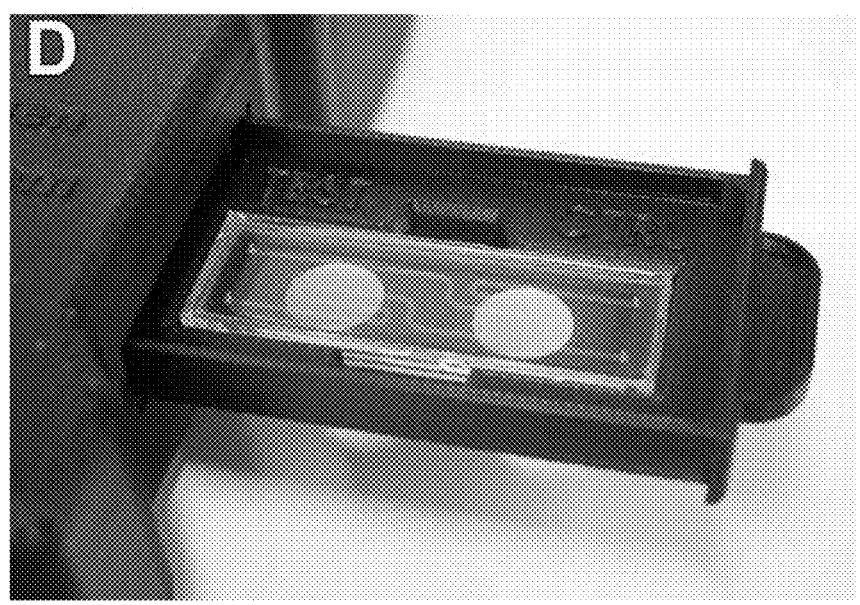

FIG. 4 shows examples of Mie light scattering curves: two "control" curves (sample matrix, unbound microparticles) and a "sample" curve (agglutinated microparticles). The present invention is not limited to the methods, reagents, and configurations described in the example shown in FIG. 4; the simulation in FIG. 4 is for example purposes only.

The solid line in FIG. 4 shows a simulated light scattering curve of the sample matrix/lettuce particles (ground lettuce after filtering with KimWipe) at $\lambda=650$ nm. For the sample matrix/lettuce particles, given that the refractive index n of a typical plant cell wall is reported as 1.425, a refractive index n of 1.425 was assigned. The particle size d was approximately 0.77 µm and the concentration was 0.1433 spheres µm$^3$. The average particle size of the lettuce particles and concentration was determined by analyzing a compilation of 9 sequential microscope images using ImageJ (National Institutes of Health, Bethesda, Md.). Cells were stained using toluidine blue (1%, w/v aqueous solution, RICCA Chemical Company, Arlington, Tex.) with standard staining procedures. The particle diameter was assumed to be nearly spherical for simulation studies. The light scattering curve for the sample matrix (lettuce) was calculated using Mie scattering equations, e.g., online software (Prahl, S., 2007, Mie Scattering Calculator, Oregon Medical Laser Center, Beaverton, http://omlc.ogi.edu/calc/mie_calc.html) with parameters of particle diameter, refractive index of medium (water, 1.333), real and imaginary refractive indices of microparticles and plant cellular debris, wavelength of incident light, and concentration of suspension. Mie scattering equations are described above and are well known to one of ordinary skill in the art.

In FIG. 4, the "maximum light scattering intensity" of the sample matrix (lettuce) is found to be at an angle ($\theta$) of approximately 38 degrees; thus, the "maximum scattering angle" for this particular simulated sample matrix (lettuce) is 38 degrees.

The dashed line in FIG. 4 shows a simulated light scattering curve for 920 nm unbound microparticles (e.g., the beads conjugated with antibody but not bound to a target microorganism). The unbound microparticles were constructed from polystyrene, thus a refractive index n of 1.59 was assigned. The particle size d was approximately 0.920 µm and the concentration was 0.1433 spheres µm$^3$. As above, the light scattering curve for the unbound microparticles was calculated using Mie scattering equations, e.g., online software (Prahl, S., 2007, Mie Scattering Calculator, Oregon Medical Laser Center, Beaverton, http://omlc.ogi.edu/calc/mie_calc.html).

In FIG. 4, the "maximum light scattering intensity" of the unbound microparticles is found to be at an angle ($\theta$) of approximately 52 degrees; thus, the "maximum scattering angle" for this particular simulated unbound microparticles sample is 52 degrees.

A triplet model (see dotted line in FIG. 4) was used to simulate agglutinated microparticles (e.g., microparticles bound to microorganism). The triplet model for representing the agglutination in the simulations was based on microscopic images of immunoagglutinated particles in the presence of *E. coli* where the triplets were the most significant. The simulation in FIG. 4 takes into account the decrease in particle concentration from agglutination (the triplet model results in ⅓ the particle concentration as compared to the singlet model, which is the unbound microparticles). The dotted line in FIG. 4 shows the simulated light scattering curve for 920 nm agglutinated microparticles. The refractive index n of 1.59 was assigned. The particle size d was approximated to be 1.6 to 1.7 µm and the concentration was 0.04766 spheres µm$^3$. As above, the light scattering curve for the agglutinated microparticles was calculated using Mie scattering equations, e.g., online software (Prahl, S., 2007, Mie Scattering Calculator, Oregon Medical Laser Center, Beaverton, http://omlc.ogi.edu/calc/mie_calc.html).

In FIG. 4, the "maximum light scattering intensity" of the agglutinated microparticles is found to be at an angle ($\theta$) of approximately 46 degrees; thus, the "maximum scattering angle" for this particular simulated agglutinated microparticles sample is 46 degrees.

For each food, a customized angle ($\theta$) may be chosen for experiments (based on simulations) so as to allow for the detection of agglutinated microparticles (as opposed to detection of the sample matrix or detection of unbound micro particles).

Referring to the example in FIG. 4, the maximum light scattering intensity of the sample matrix is detected at approximately 38 degrees, and the maximum light scattering intensity of the unbound microparticles is detected at approximately 52 degrees. The maximum light scattering intensity of the agglutinated microparticles is detected at approximately 46 degrees. In some embodiments, for actual experiments, an angle ($\theta$) is selected wherein the angle ($\theta$) is different than the maximum scattering angle of the sample matrix and the maximum scattering angle of the unbound microparticles. In some embodiments, for actual experiments, an angle ($\theta$) is selected wherein the angle ($\theta$) has a light scattering intensity for the agglutinated microparticles that is greater than both the light scattering intensity for the sample matrix and the light scattering intensity for the unbound microparticles at that angle ($\theta$).

In some embodiments, the system may be customized (e.g., parameters manipulated). For example, the system may be customized so that an angle (θ) can be chosen for experiments wherein the angle (θ) is different than the maximum scattering angle of the sample matrix and the maximum scattering angle of the unbound microparticles, or the angle (θ) has a light scattering intensity for the agglutinated microparticles that is greater than both the light scattering intensity for the sample matrix and the light scattering intensity for the unbound microparticles at that angle (θ), etc. For example, in some embodiments, one or more parameters (e.g., particle size d, wavelength λ) may be changed, thereby changing the Mie light scattering curve and possibly enabling an angle (θ) to be chosen as described herein. In some embodiments, parameters (e.g., particle size (d), the angle of light scattering detected (θ), the wavelength of incident light (λ), the refractive index of the beads (n)—the refractive index of the beads can be changed by selecting beads of different composition, e.g., titanium beads, etc.) are manipulated for customization. For example, a user may decide a range of θ, e.g., between 30 and 60 degrees, and subsequently manipulate d, λ, and/or n. In some embodiments, the wavelength λ is 375 nm, 470 nm, 650 nm, etc. In some embodiments, the particle diameter d is 510 nm, 920 nm, etc.

As previously discussed, in some embodiments, for actual experiments, an angle (θ) is selected wherein the angle (θ) has a light scattering intensity for the agglutinated microparticles that is greater than both the light scattering intensity for the sample matrix and the light scattering intensity for the unbound microparticles at that angle (θ). In some embodiments, an angle (θ) is selected wherein the angle (θ) has a light scattering intensity for the agglutinated microparticles that is at least 10% greater than both the light scattering intensity for the sample matrix and the light scattering intensity for the unbound microparticles at that angle (θ). In some embodiments, an angle (θ) is selected wherein the angle (θ) has a light scattering intensity for the agglutinated microparticles that is at least 25% greater than both the light scattering intensity for the sample matrix and the light scattering intensity for the unbound microparticles at that angle (θ). In some embodiments, an angle (θ) is selected wherein the angle (θ) has a light scattering intensity for the agglutinated microparticles that is at least 50% greater than both the light scattering intensity for the sample matrix and the light scattering intensity for the unbound microparticles at that angle (θ). In some embodiments, an angle (θ) is selected wherein the angle (θ) has a light scattering intensity for the agglutinated microparticles that is at least 75% greater than both the light scattering intensity for the sample matrix and the light scattering intensity for the unbound microparticles at that angle (θ). In some embodiments, an angle (θ) is selected wherein the angle (θ) has a light scattering intensity for the agglutinated microparticles that is at least 100% greater than both the light scattering intensity for the sample matrix and the light scattering intensity for the unbound microparticles at that angle (θ). In some embodiments, an angle (θ) is selected wherein the angle (θ) has a light scattering intensity for the agglutinated microparticles that is at least 125% greater than both the light scattering intensity for the sample matrix and the light scattering intensity for the unbound microparticles at that angle (θ). In some embodiments, an angle (θ) is selected wherein the angle (θ) has a light scattering intensity for the agglutinated microparticles that is at least 150% greater than both the light scattering intensity for the sample matrix and the light scattering intensity for the unbound microparticles at that angle (θ). In some embodiments, an angle (θ) is selected wherein the angle (θ) has a light scattering intensity for the agglutinated microparticles that is at least 175% greater than both the light scattering intensity for the sample matrix and the light scattering intensity for the unbound microparticles at that angle (θ).

As previously discussed, in some embodiments, the angle (θ) used by the light detection components 230 to detect forward scattered light may be an angle (θ) that is different from the maximum scattering angle of the sample matrix and the maximum scattering angle of the unbound microparticles. For example, in some embodiments, an angle (θ) is selected wherein the angle (θ) is both (a) at least 5 degrees more or 5 degrees less than the maximum scattering angle of the sample matrix and (b) at least 5 degrees more or 5 degrees less than the maximum scattering angle of the unbound microparticles. In some embodiments, an angle (θ) is selected wherein the angle (θ) is both (a) at least 4 degrees more or 4 degrees less than the maximum scattering angle of the sample matrix and (b) at least 4 degrees more or 4 degrees less than the maximum scattering angle of the unbound microparticles. In some embodiments, an angle (θ) is selected wherein the angle (θ) is both (a) at least 3 degrees more or 3 degrees less than the maximum scattering angle of the sample matrix and (b) at least 3 degrees more or 3 degrees less than the maximum scattering angle of the unbound microparticles. In some embodiments, an angle (θ) is selected wherein the angle (θ) is both (a) at least 2 degrees more or 2 degrees less than the maximum scattering angle of the sample matrix and (b) at least 2 degrees more or 2 degrees less than the maximum scattering angle of the unbound microparticles.

In some embodiments, for a new food, a user can choose from several different ways of collecting a sample. In some embodiments, the sample is a fluid used to wash the food sample (e.g., a buffer used to wash lettuce leaves). In some embodiments, the sample is a fluid sample, e.g., fluid from a package of chicken. In some embodiments, the sample is a ground or mashed food (e.g., ground berry, ground lettuce, etc.). In some embodiments, the sample is filtered. In some embodiments, the sample is diluted.

In some embodiments, the user can optionally look at the size of the food debris via a microscope (as described above with respect to FIG. 4). The refractive index, n, can typically be obtained from literature. A user may choose to run a simulation experiment or an actual experiment, similar to the simulation shown in FIG. 4 with simulated lettuce.

Sensitivity and Thresholds

In some embodiments, the sensitivity of the system is 10 CFU/ml. Converting a level of microorganism, e.g., 10 CFU/ml, to a level of microorganism in the whole food sample can sometimes be difficult. For example, if a lettuce sample is used, it can be diluted or ground in various amounts of buffer, or the lettuce can be washed with fluid and the fluid used as the sample. Thus, a user can opt to define his/her own terms/parameters and procedures for creating a way to compare various samples of the same food (e.g., creating a standard curve, a standard threshold, etc.). For example, a user may choose to always dilute 10 grams of lettuce into 10 ml of buffer. Or, a user may choose to always wash 10 grams of lettuce with 10 ml of buffer, the buffer being what is used as the sample.

Customization of Microfluidic Device

In some embodiments, the distance between the test channel 170 and the light device 220 (or light conduit 228) is fixed. In some embodiments, the distance between the test channel 170 and the light detection component 230 (or light conduit 328) is fixed. In some embodiments, the focal point is fixed. In some embodiments, the angle ($\theta_1$, $\theta_2$) is fixed. In some embodiments, the system allows for manipulation (or fine tuning) of the distance between the test channel 170 and the light device 220 or light conduit 228 or light detection component 230 or light conduit 328. In some embodiments, the focal point can be manipulated. In some embodiments, the angle ($\theta_1$, $\theta_2$) can be manipulated.

In some embodiments, the system 100 is cooled adequately before a test is run. In some embodiments, the system 100 is programmed to collect data during a certain time interval (e.g., less than about 20 seconds, less than about 30 seconds, less than about 40 seconds, less than about 50 seconds, less than about 60 seconds) and then automatically shut off, e.g., so as to allow the system 100 to cool. In some embodiments, a blank tray is used to measure a baseline signal before samples are tested, e.g., if the baseline signal is greater than 0 then the system is allowed to cool further.

To decrease noise, a user can opt to decrease noise via hardware or software. For example, in some embodiments, a user employs noise-filtering algorithm software, which processes digital data from the system. In some embodiments, a user employs a noise filtration chip, e.g., a digital signal processing chip (DSP chip). The DSP chip outputs already processed digital data. DSP chips are well known to one of ordinary skill in the art.

Generally, when the detector 230 (or light conduits 328) detects light at the angle with respect to the incident light/sample/test region 170, there is a small acceptance angle. For example, in some embodiments, when the detector 230 is detecting light at a X degree angle, the detector may actually be detecting light at X degrees +/−1 degree, +/−2 degrees, +/−3 degrees, +/−4 degrees, etc. In some embodiments, a user can decrease the acceptance angle (e.g., to go from X degrees +/−4 degrees to X degrees +/−2 degrees. In some embodiments, a user decreases the acceptance angle by bringing the detector 230 (or light conduit 328) and sample or test chip 130 closer together.

Statistical Analysis

In some embodiments, a ratio of $I/I_0$ may be calculated via the system of the present invention. In some embodiments, a ratio of greater than 1 indicates the presence of the microorganism in the sample. Means (m) and standard deviations ($\sigma$) of $I/I_0$ may be collected from multiple measurements. In some embodiments, two-sigma bounds (m−2$\sigma$, m+2$\sigma$) can be obtained, wherein the lower bound (m−2$\sigma$)>1 indicates that $I/I_0$ is greater than 1 with a 95% confidence level.

In some embodiments, a difference between I and $I_0$ may be calculated via the system, e.g., by subtracting of $I_0$ from of I. In some embodiments, a difference of greater than 0 indicates the presence of the microorganism in the sample. As stated above, means (m) and standard deviations ($\sigma$) may be collected from multiple measurements. In some embodiments, two-sigma bounds (m−2$\sigma$, m+2$\sigma$) can be obtained, wherein the lower bound (m−2$\sigma$)>0 indicates that I−$I_0$ is greater than 0 with a 95% confidence level.

In some embodiments, when calculating a ratio of $I/I_0$, a ratio of greater than 1 indicates the presence of the microorganism in the sample. In some embodiments, when calculating a ratio of $I/I_0$, a difference between I and $I_0$ is calculated by subtracting of $I_0$ from of I, wherein a difference of greater than 0 indicates the presence of the microorganism in the sample.

EXAMPLES

Example 1

Conjugation of an Antibody

The following are examples of conjugating an antibody. The present invention is not limited to this example. One (1) ml of 0.02% (w/v) 0.92-µm highly carboxylated polystyrene (HCPS) particles (e.g., 10 carboxyl groups per 1 $nm^2$ particle surface; Bangs Laboratories, Fishers, Ind.) can be conjugated with 1 ml of 1.023 µg/ml anti-*E. coli* (e.g., polyclonal antibody developed in rabbit; catalog number ab13626; Abcam, Cambridge, Mass.) via physical adsorption. Surface coverage of antibodies to particles may be about 33%.

In some embodiments, 920 nm mean diameter, high-acid content, poly (styrene/15% acrylic acid) latex microparticles (Bangs Laboratories, Inc. Fishers, Ind.) may be conjugated with the antibody. In some embodiments, the antibody is rabbit anti-*E. coli* K12 (Sigma-Aldrich, St. Louis, Mo.). In some embodiments, the antibody is a rabbit anti *E. coli*) O157:H7 (Meridian Life Sciences, Inc. Saco, Me.). Protocols for conjugating the microparticles may be found in Heinze et al., 2010, Anal. Bioanal. Chem. 398, 2693-2700).

Example 2

Culturing of *Escherichia coli*

The following is an example of culturing *Escherichia coli*. The present invention is not limited to this example. *E. coli* K-12 lyophilized cell powder (Sigma-Aldrich catalog number EC1) can be cultured in media, for example brain heart infusion broth (Remel, Lenexa, Kans.), at about 37° C. for about 20 h. The grown cell culture of lyophilized *E. coli* K-12 can be serially diluted with 10 mM PBS (pH 7.4) by $10^{-5}$ to $10^{-8}$. As the lyophilized powder of *E. coli* K-12 may contain dead cell fragments and free antigen, the diluted *E. coli* K-12 solutions can be washed by centrifuging at about 2000 g for about 15 min, followed by elimination of supernatants and resuspension in PBS. This centrifugation-resuspension can be repeated (e.g., 3 times) to help ensure complete removal of dead cell fragments and free antigens.

A viable cell count can be performed by planting dilutions (e.g., abut 200 µl) to eosin methylene blue agar (DIFCO, Lawrence, Kans.) and incubating at about 37° C. for about 20 h. To stain viable and non-viable cells, SYTO 9 and propidium iodide (LIVE/DEAD BacLight viability kit; Invitrogen, Carlsbad, Calif.) can be used following the protocol as described in manufacturer's product information (Molecular Probes, 2004). Stained *E. coli* cells can be observed with a fluorescent microscope (Nikon, Tokyo, Japan). Cells can be counted using a Petroff-Hausser counting chamber (Electron Microscopy Sciences, Hatifield, Pa.).

Example 3

Vegetable Sample Preparation

The following is an example of vegetable sample preparation. The present invention is not limited to this example (e.g., the samples do not necessarily need to be filtered with a filter or KimWipe or the like, e.g., if there are no large pieces, etc.). Iceberg lettuce is chopped up using a grinding bowl. Phosphate buffered saline (PBS; 100 mM) is added to this ground iceberg lettuce at the ratio of 2:1 (buffer:lettuce). If the lettuce is not contaminated with *E. coli*, a known amount of *E. coli* may be added to PBS. This mixture is loaded in a 1 ml disposable syringe. KimWipes, delicate task wiper, is placed onto the outlet of a syringe, without a needle. Big vegetable particles (but not *E. coli*) are filtered with KimWipes, by injecting the plunger of a syringe. The filtered sample is loaded into a channel of a test slide.

Example 4

Simulation with Plant Tissue Sample

The follow example describes simulation experiments performed to determining the effect of plant tissue on light scattering. Iceberg lettuce was ground and filtered with a KimWipes general task wiper (pulp and very large particles were removed). FIG. 4 shows the Mie scatter properties of the aforementioned filtered lettuce particles (refractive index, n, =1.425), 920 nm microparticles (n=1.59) as singlets representing a sample without the microorganism (e.g., no agglutination) and 920 nm microparticles (n=1.59) as triplets representing a sample with the microorganism (e.g., agglutination). The simulation accounts for the decrease in particle concentration from agglutination; thus the triplet model results in ⅓ the particle concentration as compared to the singlet model. At a forward scattering angle of 45 degrees, the 920 nm singlet shows a minimal increase in light scatter intensity over the lettuce particles, and the 920 nm triplet shows a significant increase over the lettuce particles as well as the 920 nm singlet. This simulation demonstrates that the detection of a microorganism in a real biological matrix under these minimal pretreatment steps for iceberg lettuce is possible, e.g., by choosing an appropriate scattering angle.

Example 5

Customization of Wavelength and Particle Size

The wavelength of the light and/or the microparticle size may be customized for the particular sample that is being tested. For example, in some embodiments, the light (e.g., first incident light, second incident light) has a wavelength of about 650 nm when the sample is lettuce.

Figure 6A:
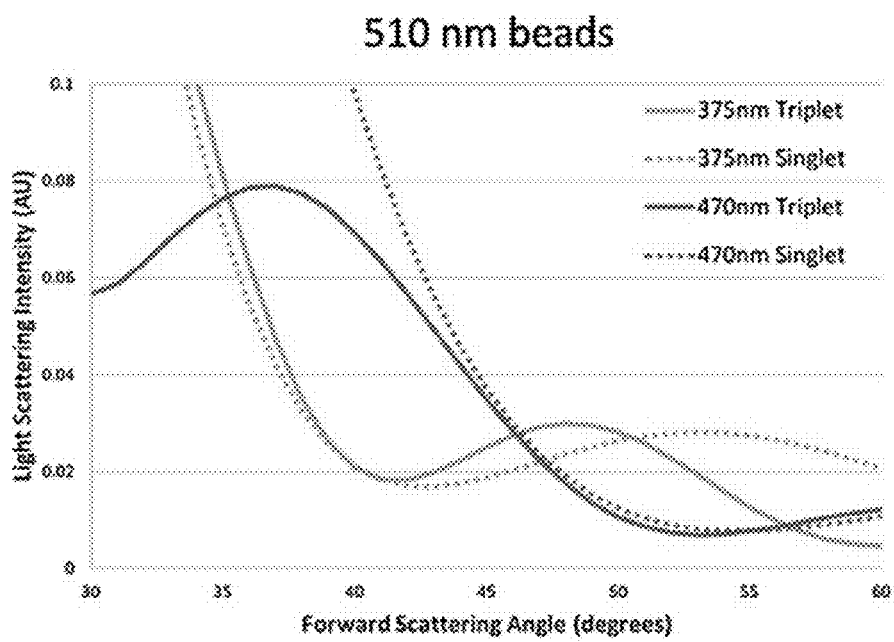
FIG. 6A shows Mie scatter simulations obtained with 510 nm microparticles with a 375 nm UV light source and a 470 nm blue light source. The singlets represent a sample without the microorganism (e.g., no agglutination), and the triplets represent a sample with the microorganism (e.g., agglutination).
Figure 6B:
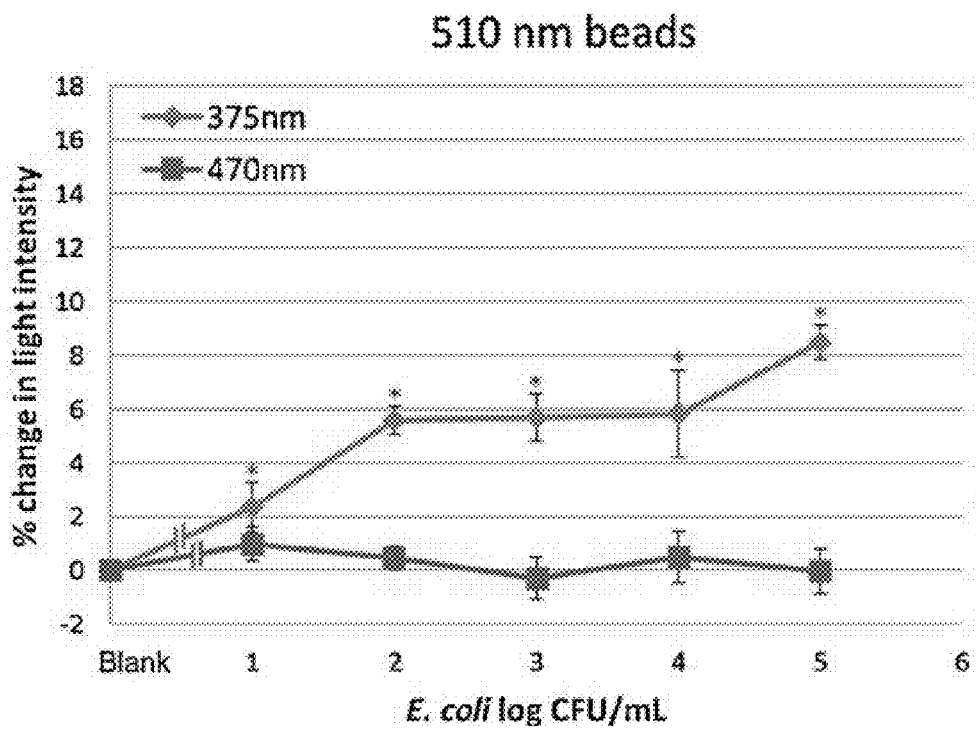
FIG. 6B shows experimental results obtained with the 510 nm microparticles with a 375 nm UV light source and a 470 nm blue light source.
Figure 6C:
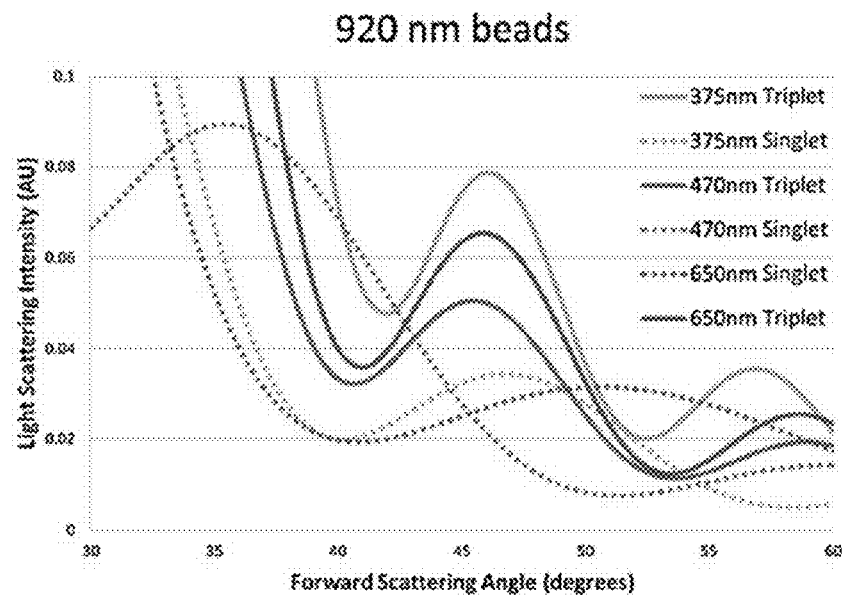
FIG. 6C shows Mie scatter simulations obtained with 920 nm microparticles with a 375 nm UV light source, a 470 nm blue light source, and a 650 nm red light source. The singlets represent a sample without the microorganism (e.g., no agglutination), and the triplets represent a sample with the microorganism (e.g., agglutination).
Figure 6D:
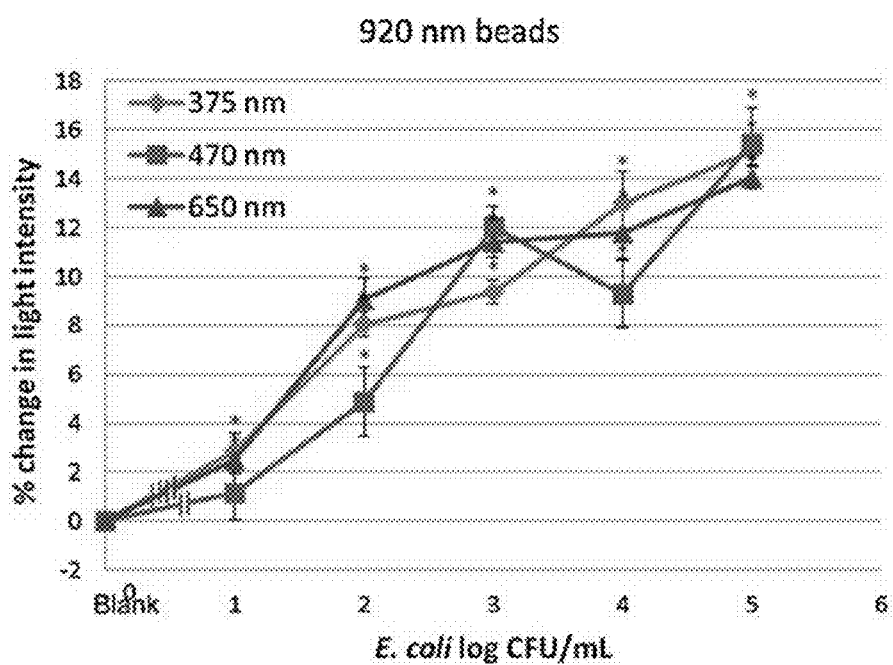
FIG. 6D shows experimental results obtained with the 920 nm microparticles with a 375 nm UV light source, a 470 nm blue light source, and a 650 nm red light source.

FIG. 6A shows Mie scatter simulations obtained with 510 nm microparticles with a 375 nm UV light source and a 470 nm blue light source. FIG. 6B shows experimental results obtained with the 510 nm microparticles with a 375 nm UV light source and a 470 nm blue light source. FIG. 6C shows Mie scatter simulations obtained with 920 nm microparticles with a 375 nm UV light source, a 470 nm blue light source, and a 650 nm red light source. FIG. 6D shows experimental results obtained with the 920 nm microparticles with a 375 nm UV light source, a 470 nm blue light source, and a 650 nm red light source. The singlets in FIG. 6A and FIG. 6C represent a sample without the microorganism (e.g., no agglutination), and the triplets in FIG. 6A and FIG. 6C represent a sample with the microorganism (e.g., agglutination).

The experimental results with the 510 nm microparticles show a moderate difference in percent change in intensity with the 375 nm light source over the 470 nm light source. And, the simulations with the 510 microparticles for 375 nm show a moderate increase in scatter intensity at 45 degrees between the singlet and triplet models, and no increase in scatter intensity for the 470 nm. The experimental results for the 920 nm microparticles show that the 375 nm, 470 nm, and 650 nm wavelengths produce large intensity changes. However, while all three wavelengths showed high sensitivity, the 650 nm wavelength exhibited the least variation, which can be explained through the slopes of the singlet models for each wavelength. For 470 nm, 45 degrees falls on an anti-node, making it the most sensitive to changes in particle size (and angle). At 375 m, the slope decreases significantly, and at 650 nm, the slope broadens out even further. Thus, while 375 nm had the largest increase in scatter intensity, 650 nm exhibited the least signal variation.

Example 6

Positive Standard Curve and Negative Control

Figure 7:
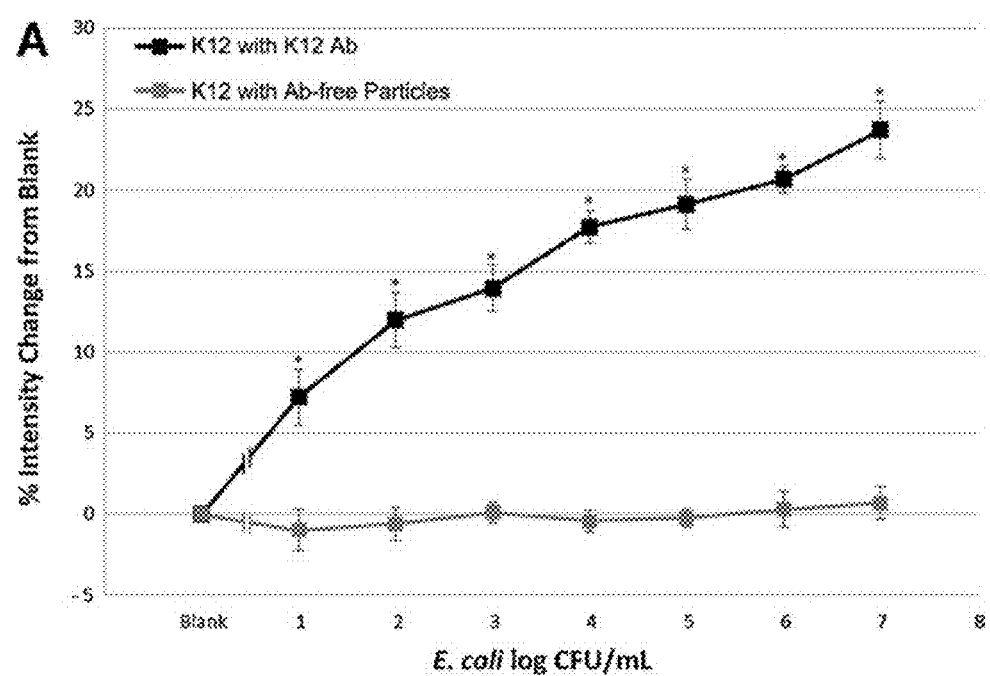
FIG. 7 shows a positive standard curve obtained using *E. coli* K12 and *E. coli* K12-conjugated beads, and a negative control curve using *E. coli* K12 and antibody-free beads.

The system of the present invention may utilize standard curves, e.g., a positive standard curve. FIG. 7 shows the positive standard curve obtained using *E. coli* K12 and *E. coli* K12-conjugated beads, and the negative control curve using *E. coli* K12 and antibody-free beads. The results show good linearity with a limit of detection of 10 CFU/ml with good statistical significance ($p<0.05$) over blank. Linearization of the calibration curve for the system 100 of the present invention may be an essential requirement for field applications.

Because of the size of the microfluidic channels of the system 100 of the present invention, the samples/mixtures exhibit laminar flow, in which diffusion (e.g., axial diffusion) is the predominant mode of particle mixing. During injection into the microfluidic channel, the velocity profile of the cross-sectional area induces agglutinated particles of a smaller mean diameter to move toward the center where the velocity is greater, whereas the larger agglutinated particles move primarily along the walls where the velocity is lower. Thus, the agglutinated particles adopt a form of temporal history in which the smaller particles with reach the detection region at a different time than the larger particles. This may be observed as a slight decrease in signal intensity, evident in the concentrations exhibiting a greater difference in particle size variation (e.g., CFU/ml=$10^3$, CFU/ml=$10^4$). Due to the time sensitive nature of particle immunoagglutination assays, the control of time-wise measurements by the system may be an essential design criterion. The averaged intensity measurement over a consistent time scale may improve assay reproducibility/linearity and crease sensitivity by observing a broader temporal filed of agglutinated particles.

Example 7

Sample Preparation Comparison

Figure 8:
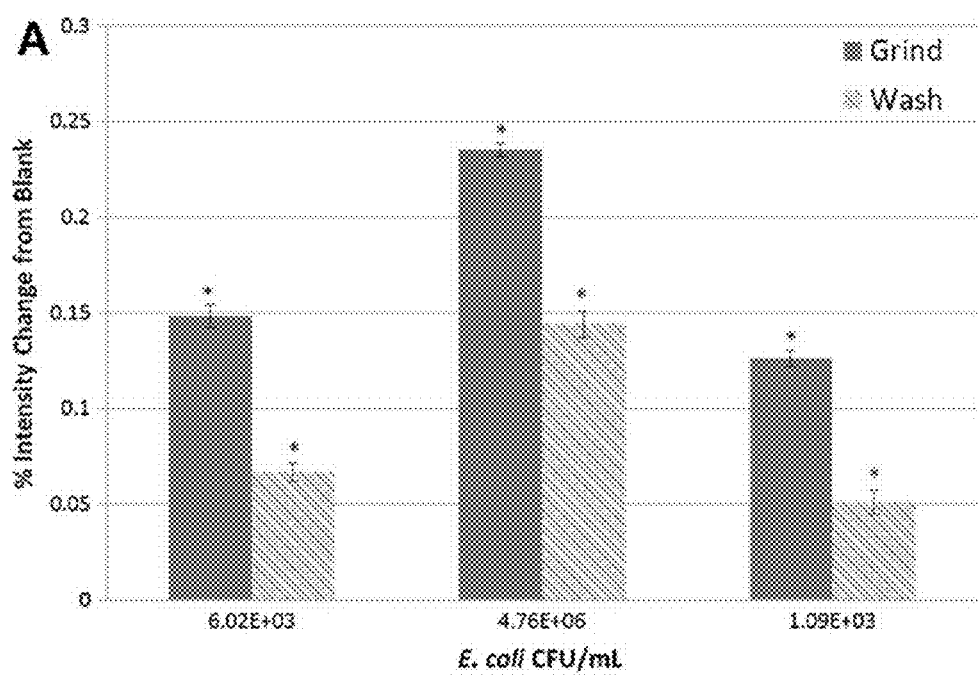
FIG. 8 shows the results of three experiments comparing iceberg lettuce samples prepared via grinding or via washing.

The following example describes two sample (iceberg lettuce) preparation methods. Two preparation methods were investigated: grinding and washing. A portion of a sample of iceberg lettuce with *E. coli* cultured directly onto its surface was ground in a mortar and pestle. A portion of the aforementioned sample was washed in PBS. FIG. 8 shows the result of a simulated field study of three independent trials comparing the two methods of preparation. The concentration values were calculated based on the standard curve generated in FIG. 7. The variation in intensity change from trial to trial was due to different lettuce samples and slightly different incubation times. The grinding method has a consistent improvement in percent change of signal intensity over blank, with an average improvement of two-fold over washing. Although grinding the lettuce samples yielded higher sensitivity, it came at the cost of longer assay time with additional equipment required (e.g., mortar and pestle, KimWipes filter), e.g., the washing protocol took approximately 1 minute and the grinding protocol took approximately 5 minutes. Thus, as a field application, the washing protocol may be a better fit.

Example 8

Photodiode and Light Source Circuit

The following example describes examples of the photodiode and light source circuitry. In some embodiments, the differential voltage signal from the avalanche photodiodes are amplified and conditioned through multiple operational amplifier stages (op-amp), processed with an analog to digital converter (ADC) (e.g., 24-bit), and statistically analyzed by the microcontroller/microprocessor software. In some embodiments, the entire amplifier circuit is powered through an ICL 7660 CMOS switched-capacitor voltage converter (e.g., obtained from Digi-Key Corporation, Thief River Falls, Minn.), for powering the op-amps. In some embodiments, the positive and negative voltage sources feed the five TL082P operational amplifiers, each with a gain of 10, and a zero adjust stage with a 20 kΩ potentiometer. In some embodiments, the op-amp circuit outputs the amplified differential voltage between the two APDs into an LTC2400 24-bit ADC, which utilizes an LT1021-5 5 V reference voltage IC (Digi-Key Corporation). The digital signal then feeds into the microcontroller for data processing and output.

In some embodiments, the entire APD and light source circuit is constructed on one double-sided photoresist coated copper clad circuit board. Circuit boards, resist etching solution, and ferric chloride solution may be obtained from Marlin P. Jones & Assoc. (MPJA; Lake Park, Fla.). Circuit design, customization, and trace routing may be performed in FreePCB (Free Software Foundation, Inc., Boston, Mass.) and printed onto clear transparencies using a 2400 dpi laser printer. In some embodiments, the coated copper-clad board is then exposed to an incandescent 100 W bulb and dissolved in photoresist developer (MPJA) at 46° C. for 6 min. The board may be then transferred to 0.240 g mL−1 ferric chloride bath (MPJA) at 55° C. for 10 min. Remaining photoresist may be removed using pure anhydrous acetone and drilled with a 0.025 inch (0.635 mm) bit.

Example 9

Test Slide Preparation

The master mold for the test slide may be constructed using standard photolithography methods. In some embodiments, SU-8 resist (MicroChem Corp., Newton, Mass.) is spin-coated onto glass slides, exposed by UV using an ABM Mask Alignment System (ABM, Inc., Scotts Valley, Calif.) over a chrome mask created with a Heidelberg Micro PG 101 Direct Write System (Heidelberg Instruments Mikrotechnik GmbH, Tullastrasse, Heidelberg, Germany), and developed. Polydimethylsiloxane (PDMS) may be poured onto the positive master mold and cured in a convection oven, e.g., for 1 h. The PDMS may then be peeled off of the master mold, revealing two channels, and bonded to a glass slide via oxygen plasma treatment, e.g., for 2 min (Plasma Preen Cleaner/Etcher; Terra Universal, Fullerton, Calif.). Teflon tubing and a syringe attached to the channel inlets may be used to fill and evacuate the chamber.

Example 10

Assay for *Salmonella* in Poultry Package Water

A handheld optical immunoassay device was used to detect *Salmonella typhimurium* in the naturally occurring water from poultry packages (hereinafter "chicken matrix") with a single pipetting of a sample. For example, no pipetting was required for reagents and a separate negative control, and no filtration/purification was required.

Various concentrations of *Salmonella* were spiked into PBS, 10% or 1% chicken matrix (PCR-negative). Carboxylated, polystyrene nanoparticles were covalently conjugated with anti-*Salmonella* antibodies. The presence of *Salmonella* resulted immunoagglutination of particles that could be quantified by measuring forward light scattering in a two-channel microfluidic device. A handheld device was fabricated to read the scatter signals.

Figure 9A:
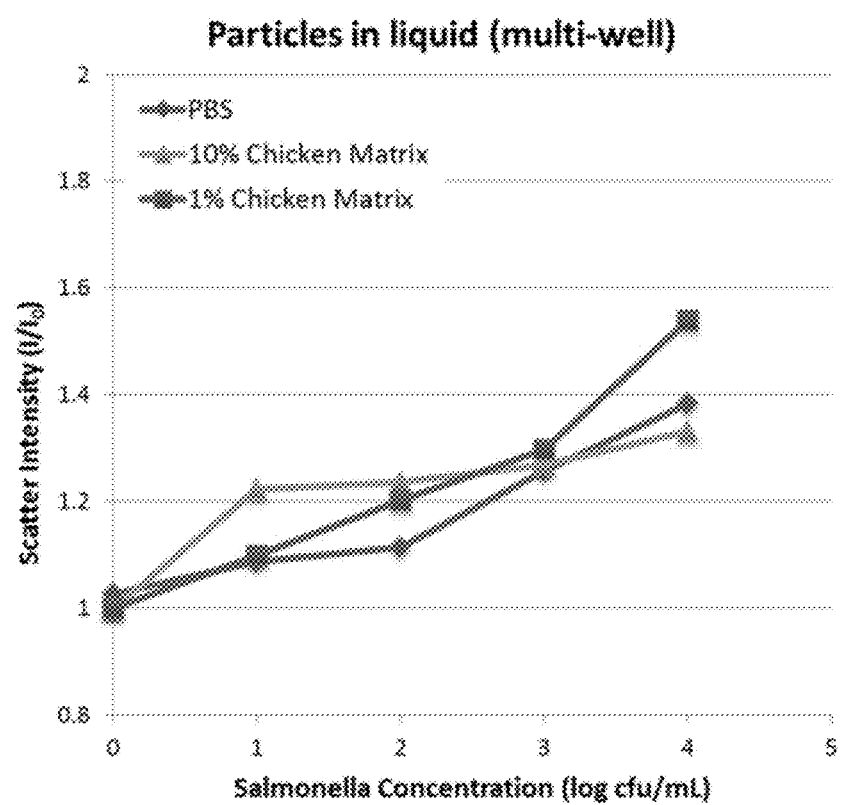
FIG. 9A shows normalized light scatter intensities against the log *Salmonella* concentrations in three different sample matrices, using antibody-conjugated particles in liquid suspension in a multi-well slide. Standard error=0.06-0.16.
Figure 9B:
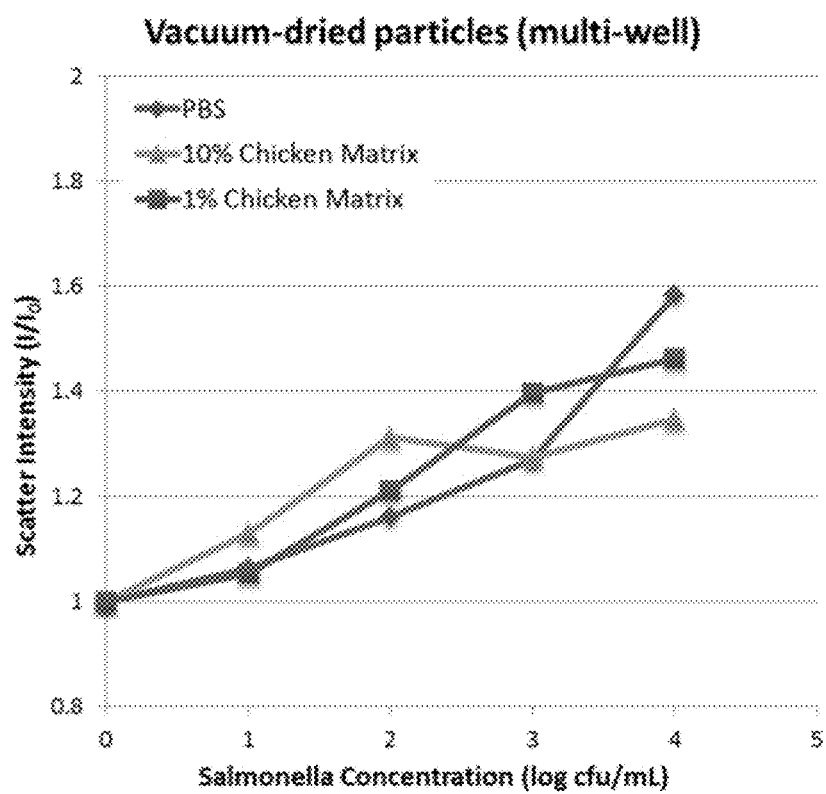
FIG. 9B shows the same experiment in FIG. 9A but with vacuum-dried particles. Standard error=0.09-0.16.

FIG. 9A shows a plot of normalized scattered light intensity against the log of *Salmonella* concentration using the particles in liquid suspension with surfactant. The presence of chicken matrix did not affect the light scatter signal, since the optical parameters (d, λ and θ) were customized to minimize the effect of sample matrix (see previous discussion of customization of d, λ and θ). This experiment was repeated with vacuum-dried particles (see FIG. 9B), showing the same trend. To further simplify the assay, a two-channel microfluidic device (FIG. 10) was fabricated and tested. Only a single pipetting of sample was needed, which split into two channels, one with antibody-conjugated and the other with non-antibody-conjugated particles, both vacuum-dried within the channels. FIG. 11A shows the results, indicating the ability to simultaneously detect target and negative control signals. FIG. 11B shows the results of a long-term storage study, indicating stable signals (in lower *Salmonella* concentrations) up to 6 weeks. For this particular experiment, with 10% chicken matrix, the limit of detection was 10 CFU/mL and the linear range of assay was up to $10^6$ CFU/ml.

Example 11

*Salmonella* in Poultry Package Water

The following example describes experiments testing *Salmonella* levels in poultry package water and determining shelf life of lyophilized reagents in the test slide (130).

The *Salmonella typhimurium* Z005 strain (ZeptoMetrix, Buffalo, N.Y., USA) was cultured in 25 mg mL−1 brain heart infusion broth (Remel, Lenexa, Kans., USA). It was incubated for 12 hours at 37° C. with the final concentration of 8.6×$10^8$ CFU mL-1. 10 mL brain heart infusion broth was used for culturing. This bacterial culture (assumed $10^9$ CFU mL−1) was used to make serial dilutions in 50 mM pH 7.4 phosphate buffered saline (PBS).

Fresh chicken thighs were purchased from local stores. The fresh liquid was extracted from the packaging with no further processing. The extracted liquid samples were confirmed to be negative for K005 using standard cell plating techniques. The raw samples were then used to make 10% and 1% dilutions in 50 mM PBS. In this example, the testing matrices will be termed PBS, 1%, and 10% chicken matrix. 2 mL aliquots of these matrix dilutions were placed in centrifuge tubes and refrigerated until use, and they were monitored daily and never used after 4 weeks. For testing, the sample matrices were spiked with the serially diluted *S. typhimurium* to the appropriate ratios, ensuring that the sample matrix was not further diluted. The spiked samples were placed in 2 mL centrifuge tubes at room temperature during testing.

A microfluidic system/device/apparatus of the present invention with a 650 nm laser diode light source and detectors set at 45° was used. The case of the apparatus was designed using SolidWorks 2010 (SolidWorks Corp., Concord, Mass., USA). The casing was printed in acrylonitrile-butadiene-styrene (ABS) using a Dimension 1200ES 3D printer (Stratasys, Inc., Eden Prairie, Minn., USA). The APDs were kept in dark conditions during testing. To achieve light scattering of the immunoagglutinated polystyrene latex particles, two 3 mm laser diodes (7 mm collimating lenses) (Lasers4U, Co. Walnut Creek, Calif., USA) were placed directly below the "viewing" areas of the test slide. Two UV-Vis silicon APDs (Edmund Optics, Barrington, N.J., USA) were positioned above the viewing areas of the chip to detect the scattering intensity, and the differential voltage from the APDs was amplified through a differential operational amplifier (TL-082). This is a JFET (junction field effect transistor) operation amplifier designed to work with low input current (i.e., high imput impedance). The gain was set to 200,000 with single-stage differential amplification, thus it required no zero adjustment stage. In addition, a first-order low pass filter with a cutoff frequency of 160 Hz was also added. The final output signals were read through a Rigol D21052E digital oscilloscope (Rigol Technologies, Inc., Oakwood Village, Ohio, USA). This version of a circuit was designed to reduce the noise and measurement-to-measurement variation.

The test slides (130) were fabricated in polycarbonate using micro non-circular milling equipment. Briefly, a Roland MDX 540A (Roland DG Corp., Irvine, Calif., USA) was used for the milling, and the code was generated using Surfcam 5.2 software (Surfcam, Camarillo, Calif., USA). The slides (130) contain multiple layers: the channel cutout, the bottom casing, and the top casing, which includes vents. The central layer contains HR90445 adhesive to prevent leaking.

920 nm mean diameter polystyrene latex microparticles (Bangs Laboratories, Inc., Fishers, Ind., USA) were used as the agglutination agents in the assay. Rabbit polyclonal antibodies to the *Salmonella typhimurium* group antigen (Abcam Inc., Cambridge, Mass., USA) were covalently bonded to the microparticles for 100% coverage, following a protocol used in Heinze et al. (Heinze et al., 2010, Anal. Bioanal. Chem. 398, 2693-2700). In typical immunoassays, a separate negative control is required, e.g., the same chicken matrix with no *Salmonella* target. Such a negative control can be difficult to prepare and can also require refrigeration. Therefore, "control" particles were used with the same sample (*Salmonella*-spiked chicken matrix) to obtain negative control readings. These control particles were used either without any conjugation or with bovine serum albumin (BSA) conjugation with 33% coverage following the same method.

10 µL of the anti-*Salmonella* conjugated particles were loaded in the microfluidic channel along with 0.02% (for PBS and 1% chicken matrix) or 0.04% (for 10% chicken matrix) Tween 80 surfactant solutions. In addition, 10 µL 33%-BSA-conjugated particles were loaded in the microfluidic channel, with 0.04% Tween 80. Care was taken not to mix the particles and surfactant when loading them into the microchannels. The loaded particles were dried overnight in a clean vacuum desiccator chamber (Ted Pella Inc., Redding, Calif., USA) with a 0.02 horsepower (HP) vacuum pump (Barnant Co., Barrington, Ill., USA).

A benchtop optical detection system was also used to customize parameters and collect preliminary results, which was previously described in Heinze et al. (Heinze et al., 2010, Anal. Bioanal. Chem. 398, 2693-2700). Briefly, the microfluidic/two-well chip was situated on a flat platform using three axes, and red light emitting diode (LED) light source (650 nm) (Ocean Optics, Dunedin, Fla., USA) was used to irradiate the sample. A fiber optic cable and USB4000 miniature spectrometer (Ocean Optics) were used with SpectraSuite software (Ocean Optics) to measure the light scattering intensity of the sample. For testing with vacuum dried particles, a 30 µL sample in each of the three matrices (PBS, 10% and 1% diluted chicken matrices) was introduced into the chip. The *Salmonella* concentrations in the spiked samples used for testing ranged from 0 (blank in PBS or negative control in chicken matrix) to $10^6$ CFU mL−1. For testing with liquid particles, 7 µL particles were combined with 21 µL spiked matrix liquid and 2 µL 0.02% or 0.04% Tween 80 (see section 2.4 for the Tween 80 concentrations used). The final concentration of particles in these mixtures was always set to 0.01% (w/v). In both cases, all three matrices were used, and tests included blanks (for PBS) and negative controls (for chicken matrices). Measurements of scattered light intensity were recorded, and all readings were normalized by dividing them with blanks or negative controls. Standard curves were constructed by plotting the normalized scattered light intensity against the *Salmonella* concentration. Measurements were taken once every second for up to 6 minutes using SpectraSuite software and were averaged for a certain duration of time (e.g., from 3 to 6 minutes after target injection). Measurements were taken in triplicate, and data points were averaged together to generate standard curves. For real-time monitoring of scatter intensities, the measurements were occasionally made up to 15 minutes.

The stability and shelf life of vacuum-dried, antibody-conjugated particles within the two-well chips were assessed in three conditions over a 12-week period. The conditions were tightly controlled at room temperature, refrigerated temperatures (3-8° C.) and elevated temperatures (51-55° C.) in a convection oven. Antibody-conjugated particles and 0.02% Tween 80 were loaded into the chips and vacuum dried as previously described. The loaded chips were tightly sealed and stored in their appropriate conditions. The testing matrix used was 50 mM (pH 7.4) PBS, the target *Salmonella* concentrations were 0 to $10^6$ CFU mL−1, and measurements were recorded on a benchtop system after 4, 8, and 12 weeks. Stability was determined by the signal intensity loss at each temperature with increasing time.

The handheld device was tested to demonstrate that efficient field testing is possible with the system, including the microfluidic chips pre-loaded with particles, single-pipetting of sample matrix, and no sample processing. Testing was in 10% chicken matrix, including the negative control, and 0.04% Tween 80, using the vacuum dried anti-*Salmonella* particles and 33% BSA-conjugated particles in microfluidic channels. Measurements from both channels were taken simultaneously for the duration of 12 seconds, beginning 3 minutes after the sample was introduced. The circuitry was powered off for the initial 3 minutes to avoid self-heating issues of APDs. A standard curve was generated from the data.

Shelf life is a very important aspect for particles used in field immunoassays due to limited storage conditions. For example, rather than refrigeration storage conditions, particles are more likely to be stored at room temperature or in a hot vehicle. To simulate field storage conditions, dried particles were sealed and stored at room temperature, 3-8° C., and 51-55° C. and were tested after 4, 8, and 12 weeks in PBS. Results, shown in FIG. 15A-C, show good signal increase in all storage conditions for the initial 8-week period. However, by 12 weeks, significant signal loss can be observed, and the antibodies stored in the higher temperatures appear to be completely denatured. The results suggest that the room temperature storage conditions should suffice for long-term particle storage, although caution should be taken using particles 12 weeks old since they exhibited significant signal loss.

The above experiments were also performed in a microfluidic chip, again using the same benchtop optical detection system, but this time with only vacuum-dried particles. FIG. 17A depicts the standard curves from the left side channel (anti-*Salmonella* conjugated particles) and the right side channel (unconjugated particles), using the same *Salmonella*-spiked 1% chicken matrix introduced to the shared injection point. Both signals are normalized to those with no-*Salmonella*-spiked 1% chicken matrices. The standard curve with anti-*Salmonella* conjugated particles shows a good signal increase over the range of target concentrations, while the one with unconjugated particles does not show such increase and is substantially smaller than 1. A series of t-tests were performed between these two curves, with all data points passing ($p<0.05$). These measurements were made at fixed time, usually at 3 minutes after sample introduction, but the results were somewhat unstable with substantially bigger standard errors. This instability is possibly due to the different nature and magnitude of interactions between the proteins in the matrix and the negatively charged terminal carboxyl groups on the particles.

To further stabilize and particularly "passivate" such interactions, bovine serum albumin (BSA) was conjugated to the carboxylated polystyrene particles, instead of using unconjugated particles. BSA is (relatively) inert to immunoassays and large enough to minimize many different surface-protein interactions, and thus popularly used as a passivating protein for many different immunoassays. In addition, the "incubation time" was further customized by monitoring the real-time intensities with various samples. FIG. 17B shows select real-time intensities: (1) $10^4$ CFU mL−1 *Salmonella*+33% BSA conjugated particles, (2) $10^4$ CFU mL−1 *Salmonella*+anti-*Salmonella* conjugated particles, and (3) no target+anti-*Salmonella* conjugated particles. More than 3 minutes of incubation time may be necessary depending on the sample. The target+33% BSA conjugated particles showed roughly the same scattering intensity as did the negative control (no target+anti-*Salmonella* particles), suggesting that this protocol is suitable for calibration purposes.

Using this customized incubation time and the 33% BSA conjugated particles, the experiments were re-performed and the results are shown in FIG. 17C. The results show desirable linear trends with the anti-*Salmonella* particles and no signal drift/change with the 33% BSA particles, both with much smaller standard errors compared to those of FIG. 17A.

Eliminating false positives and negatives as well as demonstrating extremely low detection limit may be important for field-testing. From the above results, the microfluidic chip with anti-*Salmonella* and 33% BSA conjugated particles vacuum-dried in each channel, along with 0.02-0.04% Tween 80 also vacuum-dried, worked satisfactorily. The single entry well for sample input allowed for single pipetting while reducing assay time. This design can allow for true parallel, simultaneous tests, further contributing to reproducibility.

These experiments were replicated using a handheld detection system as described above. This system specifically utilizes a much more sensitive light transducer, the avalanche photodiode (APD), while typical miniature spectrometers employ the linear arrays of charge-coupled device (CCD) or complementary metal oxide semiconductor (CMOS). With APDs, signals can be expected to be more stable, thus potentially maximizing sensitivity. The APDs were housed in complete darkness (within the enclosure case). To avoid self-heating and signal drift issues that are common among APDs, tests were run in reverse order, from highest to lowest target concentration (from highest to lowest voltage output). FIG. 18 shows the results of the normalized light scattering in 10% chicken matrix. Measurements were recorded in triplicate, each from a different experiment. The data shows linearity over the tested range of target concentration. The dip at the lower concentrations was not observed, suggesting that matrix proteins somehow interact with the agglutinating particles. However, the increased presence of surfactant worked to break up non-specific agglutinated complexes in the sample.

A series of t-tests were performed between the standard curve with anti-*Salmonella* conjugated particles and the one with 33% BSA conjugated particles. The lowest concentration with $p<0.05$ is 10 CFU mL−1, indicating the detection limit of this assay. The p value for 1 CFU mL−1 was 0.1. If a separate negative control (e.g., 10% chicken matrix with no *Salmonella* in it) can be provided, the 33% BSA conjugated particles may not be needed. In that case, the [average−2×standard error] for 1 CFU mL−1 is still higher than 1, indicating the detection limit of this assay. Note that the total sample volume was only 15 µL to each channel, indicating less than one viable *Salmonella* in each channel. This is not improbable, since anti-*Salmonella* can only bind to free antigens, cell fragments and dead cells. This extremely low detection limit was made possible through the use of APDs in conjunction with the simplified circuit design (FIG. 19), which uses a single-stage differential op-amp with no zero adjustment. In addition, it suggests that such a device has potential use in field-testing with extreme precision. Additional modifications may be required, such as circuitry to implement a normalizing algorithm, digital filtering, and liquid crystal display (LCD) panel with buttons.

This example has demonstrated a system for the detection of *S. typhimurium* Z005 bacteria in fresh, unprocessed chicken matrices. The results demonstrated that under proper storage conditions, the conjugated particles are viable for up to about 12 weeks.

Detection limit in the various matrices for the two-well chip was 10 CFU mL−1, and the detection limit in the microfluidic chip was the same using both systems. The entire assay time was approximately 10 minutes, including sample preparation. In some embodiments, that detection only requires antigen rather than a whole bacterial cell, and the presence of surfactant acts to "dilate" the bacterial cell walls. In some embodiments, the Tween 80 releases extra antigen from the bacteria, increasing immunoagglutination. The presence of chicken matrix did not affect light scattering because the optical parameters (d, λ and θ) were customized in order to minimize such interference. The 10% matrix required higher Tween 80 concentration due to higher interfering protein content, while the 1% matrix showed a higher signal increase over the antigen concentrations. Non-specific agglutination accounted for the slightly higher signal increase in the 1% matrix over the PBS matrix.

Because customization is possible, this system may be applied to a wide variety of pathogens in a range of matrices.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A method of detecting a level of a microorganism, the method comprising:

(a) plotting a first Mie light scattering curve of light scattering intensity versus forward scattering angle at a wavelength $\lambda_1$ for a sample matrix by providing sample matrix parameters and processing the sample matrix parameters in a standard Mie scattering equation, the sample matrix parameters include at least a particle diameter $d_1$ for the sample matrix, a particle concentration $\phi_1$ for the sample matrix, and a refractive index $n_1$ for the sample matrix, the first Mie light scattering curve comprises a first maximum light scattering intensity at a first maximum scattering angle;

(b) plotting a second Mie light scattering curve of light scattering intensity versus forward scattering angle at the wavelength $\lambda_1$ for unbound microparticles by providing unbound microparticle parameters and processing the unbound microparticle parameters in the standard Mie scattering equation, the unbound microparticle parameters include at least a particle diameter $d_2$ for the unbound microparticles, a particle concentration $\phi_2$ for the unbound microparticles, and a refractive index $n_2$ for the unbound microparticles, the second Mie light scattering curve comprises a second maximum light scattering intensity at a second maximum scattering angle;

(c) plotting a third Mie light scattering curve of light scattering intensity versus forward scattering angle at the wavelength $\lambda_1$ for agglutinated microparticles by providing agglutinated microparticle parameters and processing the agglutinated microparticle parameters in the standard Mie scattering equation, the agglutinated microparticle parameters include at least a particle diameter $d_3$ for the agglutinated microparticles, a particle concentration $\phi_3$ for the agglutinated microparticles, and a refractive index $n_2$ for the agglutinated microparticles, the third Mie light scattering curve comprises a third maximum light scattering intensity at a third maximum scattering angle;

(d) comparing the first Mie light scattering curve, the second Mie light scattering curve, and the third Mie light scattering curve;

wherein the wavelength $\lambda_1$ and the particle diameter $d_2$ are selected so as to yield an angle $\theta_1$, angle $\theta_1$ being an angle on the third Mie light scattering curve that has a light scattering intensity that is greater than both a light scattering intensity of the first Mie light scattering curve at angle $\theta_1$ and a light scattering intensity of the second Mie light scattering curve at angle $\theta_1$;

(e) providing a system (100) comprising (i) a housing (110) having a testing cavity (120); (ii) a test slide (130) insertable into the testing cavity (120) of the housing (110), the test slide (130) comprises a first channel (140*a*) and a second channel (140*b*), both channels (140) share an inlet (150), the inlet (150) is adapted to accept a sample, a first test region (170*a*) is disposed in the first channel (140*a*) and a second test region (170*b*) is disposed in the second channel (140*b*), a first lyophilized portion of microparticles (144*a*) is disposed in the first channel in between the inlet (150) and the first test region (170*a*), the first lyophilized portion of microparticles (144*a*) comprises a lyophilized portion of microparticles conjugated with an antibody specific for the microorganism, a second lyophilized portion of microparticles (144*b*) is disposed in the second channel between the inlet (150) and the second test region (170*b*), the second lyophilized portion of microparticles (144*b*) comprises a lyophilized portion of microparticles not conjugated with the antibody specific for the microorganism; (iii) a light device (220) disposed in the housing (110), the light device (220) emits an incident light through both the first test region (170*a*) and the second test region (170*b*); and (iv) a light detection component (230) disposed in the housing (110), the light detection component (230) detects light scattered in the first test region (170*a*) at a first angle and light scattered in the second test region (170*b*) at a second angle, the second angle being the same as the first angle;

(f) inserting a sample suspected of comprising the microorganism into the inlet (150), the sample diffuses through both the first channel (140*a*) and the second channel (140*b*), the sample in the first channel (140*a*) mixes with the first lyophilized portion of microparticles (144*a*) to form a first mixture and travels to the first test region (170*a*), the sample in the second channel mixes with the second lyophilized portion of microparticles (144*b*) to form a control sample and travels to the second test region (170*b*);

(g) irradiating with the light device (220) the first test region (170*a*) and the second test region (170*b*) with incident light having the wavelength $\lambda_1$;

(h) detecting with the light detection component (230) a relative intensity of forward scattered light scattered by the first mixture (I) at angle $\theta_1$ and a relative intensity of forward scattered light scattered by the control sample second mixture ($I_0$) at angle $\theta_1$, wherein the test slide is not moved in between detecting scattered light from the first mixture and the second mixture; and (i) calculating a ratio of I over $I_0$ or a difference between I and $I_0$ and comparing the ratio or difference to a standard curve to determine the level of microorganism in the sample.

2. The method of claim 1, wherein the wavelength $\lambda_1$ and the particle diameter $d_2$ are selected so as to yield an angle $\theta_1$, angle $\theta_1$ being an angle on the third Mie light scattering curve that has a light scattering intensity that is at least 10% greater than both a light scattering intensity of the first Mie light scattering curve at angle $\theta_1$ and a tight scattering intensity of the second Mie light scattering curve at angle $\theta_1$.

3. The method of claim 1, Wherein angle $\theta_1$ is both (a) at least 3 degrees more or 3 degrees less than the first maximum scattering angle of the sample matrix and (b) at least 3 degrees more or 3 degrees less than the second maximum scattering angle of the unbound microparticles.

* * * * *